US006982142B2

(12) United States Patent
Cabot

(10) Patent No.: US 6,982,142 B2
(45) Date of Patent: *Jan. 3, 2006

(54) METHODS FOR SCREENING THERAPEUTICALLY EFFECTIVE AGENTS

(75) Inventor: Myles C. Cabot, Santa Monica, CA (US)

(73) Assignee: John Wayne Cancer Institute, Santa Monica, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 412 days.

This patent is subject to a terminal disclaimer.

(21) Appl. No.: 09/201,115

(22) Filed: Nov. 30, 1998

(65) Prior Publication Data

US 2002/0160354 A1 Oct. 31, 2002

Related U.S. Application Data

(60) Provisional application No. 60/067,489, filed on Dec. 1, 1997.

(51) Int. Cl.
*G01N 33/50* (2006.01)
*G01N 33/53* (2006.01)
*G01N 33/92* (2006.01)
*C12Q 1/68* (2006.01)

(52) U.S. Cl. ............................ 435/4; 435/6; 435/7.4; 436/63; 436/71; 436/503

(58) Field of Classification Search .................. 435/4, 435/7.4, 6; 436/63, 71, 503
See application file for complete search history.

(56) References Cited

U.S. PATENT DOCUMENTS

| 5,677,337 A | 10/1997 | Wei et al. .................... 514/546 |
| 5,677,341 A | 10/1997 | Lyons ........................ 514/558 |
| 5,885,786 A | 3/1999 | Cabot ........................ 435/7.21 |

FOREIGN PATENT DOCUMENTS

| WO | WO 95/21175 A | 8/1995 |
| WO | WO 97/10817 A | 3/1997 |
| WO | WO 97/40358 A | 10/1997 |
| WO | WO 99/07855 A | 2/1999 |
| WO | WO/99/28747 | 6/1999 |

OTHER PUBLICATIONS

Mestdagh et al, "Comparative study of intracellular calcium and adenosine 3', 5'-cyclic monophosphate levels in human breast carcinoma cells sensistive or resistant to adriamycin", Biochemical Pharmacology, 1994, vol. 48, pp. 709–716.* de Chaves et al, "Elevation of Ceramide within Distal Neurites Inhibits Neurite Growth in Cultured Rat Sympathetic Neurons", Journal of Biological Chemistry, vol. 272, No. 5, pp. 3028–3035, Jan. 1997.*

Lavie et al, "Accumulation of Glucosylceramides in Multidrug–resistant Cancer Cells", Journal of Biological Chemistry, vol. 271, No. 32, pp. 19530–19536, Aug. 1996.*

Abe et al., "Metabolic Effects of Short—Chain Ceramide and Glucosylceramide on Sphingolipids and Protein Kinase C," *Eur. J. Biochem.*, 210:765–773 (1992).

Abe et al., "Structural and Stereochemical Studies of Potent Inhibitors of Glucosylceramide Synthase and Tumor Cell Growth," *Journal of Lipid Research*, 36:611–621 (1995).

Bose, R. et al., "Cermide Synthase Mediates Daunorubicin–Induced Apoptosis: An Alternative Mechanism for Generating Death Signals" *Cell* 82:405–414 (1995).

Breimer et al., "The Specific Glycosphingolipid Composition of Human Ureteral Epithelial Cells", *J. Biochem.*, 98(5):1169–1180 (1985).

Cabot et al., "Tamoxifen Retards Glycosphingolipid Metabolism in Human Cancer Cells", *FEBS Letters* 394:129–131 (Oct. 1, 1996).

Cabot, M.C. et al., "Apoptosis—A Cell Mechanism Importatn for Cytoxic Response to Adriamycin and a Lipid Metabolic Pathway That Facilitates Escape", *Breast Cancer Resistance Treatment*, vol. 46(1):Abstract 283, p. 71 (1997).

Cai, Z. et al., "Alteration of the Sphingomyelin/Ceramide Pathway is Associated with Resistance of Human Breast Carcinoma MCF7 Cells to Tumor Necrosis Factor–α–Mediated Cytotoxicity" *The Journal of Biological Chemistry*, 272:6918–6926 (1997).

Callaghan and Higgins, "Interaction of Tamoxifen with the Multidrug Resistance P–Glycoprotein," *British Journal of Cancer*, 71:294–299 (1995).

Chatterjee and Harris, "Reversal of Acquired Resistance to Adriamycin in CHO Cells by Tamoxifen and 4—Hydroxy Tamoxifen: Role of Drug Interaction with Alpha 1 Acid Glycoprotein," *Br. J. Cancer*, 62:712–717 (1990).

Cheresh et al., "Localization of the Gangliosides $GD_2$, and $GD_3$, in Adhesion Plaques and on the Surface of Human Melanoma Cells," *Proc. Nat'L Acad. Sci. USA*, 81:5767–5771 (Sep., 1984).

Chuma, S. J. et al., "Loss of Ceramide Production Confers Resistance to Radiation–induced Apoptosis," *Cancer Research* 57:1270–1275 (1997).

(Continued)

Primary Examiner—Karen A. Canella
(74) Attorney, Agent, or Firm—Hogan & Hartson LLP

(57) ABSTRACT

Methods of detecting novel therapeutically active compositions based on their ability to modulate the glycolipid metabolism and overcome multidrug resistance are described. These methods are particularly useful in screening for novel chemotherapeutic agents for the treatment of cancer, as well as chemosensitizers that are capable of enhancing the cytotoxicity of such chemotherapeutic agents. A combination of one or more of these compositions can be used in the treatment of a various cancers.

7 Claims, 18 Drawing Sheets

OTHER PUBLICATIONS

Dyatlovitskaya et al., "Sphingolipids and Malignant Growth" *Biochemistry (Moscow)* 60(6): 629–633 (Jun. 1995).

Escriba et al., "Role of Membrane Lipids on the Interaction of Daunomycin with Plasma Membranes from Tumor Cells: Implications in Drug–Resistance Phenomena," *Biochemistry*, 29:7275–7282 (1990).

Ford et al., "Structural Features Determining Activity of Phenothiazines and Related Drugs for Inhibition of Cell Growth and Reversal of Multidrug Resistance," *Molecular Pharmacology*, 35:105–115 (1988).

Hannun, Y. et al., "The Sphingomyelin Cycle and the Second Messenger Function of Ceramide", *The Journal of Biological Chemistry* 269:3125–3128 (1994).

Hannun and Obeid., "Ceramide: an Intracellular Signal for Apoptosis", *Trends Biochemical Science* 20:73–77 (1995).

Holleran et al., "Characterization of Cellular Lipids in Doxorubicin–Sensitive and –Resistant P388 Mouse Leukemia Cells" *Cancer Chemotherapy and Pharmacology* 17(1):11–15 (May 1986).

Ikushima et al., "Effects of Polyunsaturated Fatty Acids on Vincristine–Resistance in Human Neuroblastoma Cells," *AntiCancer Research*, 11:1215–1220 (1991).

Inokuchi et al., "Effects of D–Threo–PDMP, an Inhibitor of Glucosylceramide Synthetase, on Expression of Cell Surface Glycolipid Antigen and Binding to Adhesive Proteins by B16 Melanoma Cells," *Journal of Cellular Physiology*, 141:573–583 (1989).

Inokuchi et al., "Antitumor Activity Via Inhibition of Glycoshingolipid Biosynthesis" *Cancer Letters* 38:23–30 (Dec. 1987).

Inokuchi and Radin, "Preparation of the Active Isomer of 1–Phenyl–2–Decanoylamino–3–Morpholino–1–Propanol, Inhibitor of Murine Glucocerebroside Synthetase," *Journal of Lipid Research*, 28:565–571 (1987).

Jaffreézou et al., "Inhibition of Lysosomal Acid Sphingomyelinaseby Agents Which Reverse Multidrug Resistance," *Biochimica et Biophysica Acta* 1266:1–8 (1995).

Jarvis, W. D. et al., "Ceramide and the Induction of Apoptosis", *Clin. Cancer Research* 2:1–6 (1996).

Kajiji et al., "Structurally Distinct MDR Modulators Show Specific Patterns of Reversal Against P–Glycoproteins Bearing Unique Mutations at Serine," *Biochemistry*, 33(17):5041–5048 (1994).

Kirk et al., "Reversal of P—Glycoprotein—Mediated Multidrug Resistance By Pure Anti–Oestrogens and Novel Tamoxifen Derivatives," *Biochemical Pharmacology*, 48(2):277–285 (1994).

Kolesnick and Golde., "The Sphingomyelin Pathway in Tumor Necrosis Factor and Interleukin–1 Signaling", *Cell* 77:325–328 (1994).

Lavie et al., "Accumulation of Novel Sphingoid Bases in Multidrug–Resistant (MDR) Human Breast Cancer MCF–7 Cells" *Proc. Annu. Meet. Am. Assoc. Cancer Inst.* 37:A2247:XP–002100453 (1996).

Lavie et al., "Agents that Reverse Multidrug Resistance, Tamoxifen, Verapamil and Cyclosporin A, Block Glycosphingolipid Metabolism by Inhibiting Ceramide Glycosylation in Human Cancer Cells" *The Journal of Biological Chemistry* 272(3):1682–1687 (Jan. 17, 1997).

Lavie et al., "Accumulation of Glucosylceramides in Multidrug–resistant Cancer Cells", *The Journal of Biological Chemistry* 271:19530–19536 (1997).

Le Moyec et al., "Proton Nuclear Magnetic Resonance Spectroscopy Reveals Cellular Lipids Involved in Resistance to Adriamycin and Taxol by the K562 Leukemia Cell Line," *Cancer Research*, 56:3461–3467 (1996).

Lloyd et al., "Cell Surface Accessibility of Individual Gangliosides in Malignant Melanoma Cells to Antibodies Is Influenced by the Total Ganglioside Composition of the Cells," *Cancer Research*, 52:4948–4953 (Sep. 1992).

Lucci, A. et al., "Glucosylceraminde: a Marker for Multiple–Drug Resistant Cancers", *Anticancer Research* Jan.–Feb.; 18(1B) 475–480 (1998).

Madhavi and Das, "Effect of n–6 and n–3 Fatty Acids on the Survival of Vincristine Sensitive and Resistant Human Cervical Carcinoma Cells In Vitro," *Cancer Letters*, 84:31–41 (1994).

McKibbin et al, "Glycosphingolipids of Cultured Human Colon Carcinoma Cells and Their Drug–Resistant Sublines", *Biochimica et Biophysica Acta*, 958:235–246, 1988.

Michael, J. M. et al., "Resistance to Radiation–Induced Apoptosis in Burkitt's Lymphona Cells is Associated with Defective Ceramide Signaling", *Cancer Research* 57:3600–3605 (1997).

Nakamura, S. et al., "Dual Roles of Sphinoglipids in Signaling of the Escape from and Onset of Apoptosis in a Mouse Cytotoxic T–cell Line, CTLL–2", *The Journal of Biological Chemistry* 271:1255–1257 (1996).

Santana, P. et al., "Acid Sphingomyelinase–Deficient Human Lymphoblast and Mice are Defective in Radiation – Induced Apoptosis", *Cell* 86:189–199 (1996).

Wyllie, A. H. et al., "Apoptosis and Carcinogenesis", *Eur. J. Cell. Biol.* 73:189–197 (1997).

Zyad, A. et al., "Resistance to TNF–α and Adriamycin in the Human Breat Cancer MCF–7 Cell Line: Relationship to MDR1, MnSOD, and TNF Gene Expression", *Cancer Research* 54:825–831 (1994).

\* cited by examiner

METHODS FOR SCREENING THERAPEUTICALLY EFFECTIVE AGENTS

1. RELATED APPLICATIONS

This application claims the benefit under 35 U.S.C. 119(e) of U.S. application Ser. No. 60/067,489 filed Dec. 1, 1997, entitled Methods for Screening Therapeutically Effective Agents and naming Myles C. Cabot as the inventor, which is herein incorporated in its entirety by reference.

2. FIELD OF THE INVENTION

The present invention relates to methods of identifying therapeutically effective agents, in particular therapeutic agents that modulate biochemical pathways such as cellular proliferation and differentiation, and apoptosis, as well as uses thereof.

3. BACKGROUND OF THE INVENTION

More than two million new cases of cancer are reported annually in the seven major worldwide pharmaceutical marketplaces (US, Japan, Germany, Italy, France, Spain, UK) (Krul, 1994). Chemotherapy is an important part of modern clinical cancer treatment for human malignancies. However, chemotherapy frequently is ineffective due to either endogenous or acquired tumor cell resistance. Typically, the resistance is developed simultaneously to a wide range of structurally unrelated chemotherapeutic drugs with different mechanisms of action and therefore is called multidrug resistance (MDR) (Deuchards and Ling, 1989; Pastan and Gottesman, 1987). Generally, only 5–10% of new cancer cases will respond successfully to chemotherapy, and 40–45% of cancer patients will annually develop MDR to their particular chemotherapeutic regimens.

Several mechanisms can account for MDR at the molecular and cellular level. Decreased drug uptake or increased drug efflux, altered redox potential, enhanced DNA repair, increased drug sequestration mechanisms or amplification of the drug-target protein all are postulated cellular mechanisms for expression of tumor cell drug resistance to various chemotherapeutic agents. One of the most thoroughly studied mechanisms by which tumor cells acquire MDR is overexpression of a transmembrane glycoprotein, called P-glycoprotein (Pgp). Pgp is thought to act by rapidly pumping hydrophobic chemotherapeutic agents out of tumor cells, thereby decreasing intracellular accumulation of certain chemotherapeutic agents below their cytostatic concentrations. Various compounds have been identified, such as tamoxifen, cyclosporin A, and SDZ PSC 833, that are able to reverse MDR. These agents, termed MDR modulators, while not chemotherapeutic drugs themselves, are important in enhancing the cytotoxicity of chemotherapeutic agents by restoring sensitivity in an otherwise resistant setting (Fan, 1994).

A major challenge in cancer chemotherapy is to understand the molecular mechanisms by which MDR modulators reverse drug resistance. The action of MDR modulators is dependent in part on interaction with the biochemical and physiological processes that evoke the resistance phenomenon. It has been shown that some MDR modulators bind directly to Pgp (Yusa, 1989; Foxwell, 1989) and thereby interfere with binding and export of anticancer agents to the drug pump. Tamoxifen, an antiestrogen compound used in treatment of breast cancer long known for MDR modulatory properties (Fan, 1994), binds to Pgp (Callaghan and Higgins, 1995), as does the nonimmunosuppressive cyclosporine A analog, PSC 833 (Archinal-Mattheis, 1995), a potent drug resistance modulator (Gaveriaux, 1995). PSC 833 has been shown to be significantly more effective than verapamil and cyclosporine A in reversing MDR, in vitro and in vivo (Watanabe, 1995). However, it has been observed that PSC 833, unlike cyclosporine A, is a strong agonist in glycolipid metabolism and elicits ceramide formation whereas cyclosporine A does not (Lucci, 1997).

Recently, it has been suggested that the development of MDR is closely related to a unique glycosphingolipid pattern within the cancer cell. It has been shown that MDR cells, as opposed to drug-sensitive cells, display increased levels of glucosylceramide (Lavie, 1996). Subsequent findings indicate that MDR modulators may increase the cellular susceptibility to chemotherapeutic agents through regulation of ceramide metabolism in cancer cells (Lavie, 1997).

Ceramide is a well-known second messenger, stimulating specific kinases, phosphatases, and transcription factors that mediate a variety of cellular functions (Hannun, 1994; Hannun and Obeid, 1995; Jarvis, 1996). It is the backbone of all sphingolipids, including sphingomyelin, and glycosphingolipids and, thus, is subject to complex metabolic regulation. Ceramide has been reported to initiate differentiation and cell proliferation, and also is known to serve as a second messenger for apoptosis (Obeid, 1993; Pena, 1997). Ceramide is reported to be the messenger of signaling events that originate from different cell surface receptors, including interferon-γ, TNF-α, interferon-1β, CD95 (Fas/APO-1), nerve growth factor receptor, and CD28 (Testi, 1996; Symth, 1997; Haimovitz-Friedman, 1997). Ceramide also appears to be involved in the action of PKC ζ, Vav protooncogene, $1\alpha$-25-dihydroxy vitamin $D_3$, dexamethasone, ionizing radiation, and chemotherapeutic agents (Testi, 1996; Symth, 1997; Haimovitz-Friedman, 1997). There is also data suggesting that loss of ceramide production is one cause of cellular resistance to apoptosis induced by either ionizing radiation, TNF-α, or adriamycin (Chuma, 1997; Cai, 1997; Michael, 1997; Bose, 1995; Santana, 1996; Zyad, 1994; Lavie, 1997; Cabot, 1997).

Ceramide is produced by either (i) condensation of the sphingoid base sphinganine and fatty acyl-CoA by the enzyme ceramide synthase and subsequent oxidation, (ii) by degradation of sphingomyelin into phosphorylcholine and ceramide by the action of sphingomyelin-specific forms of phospholipase C, or (iii) by degradation of glucosylceramide by β-glucosidase (glucocerebrosidase). The ceramide formed then is metabolized to sphingomyelin or glucosylceramide by addition of the appropriate head group.

Glucosylceramides are the most widely distributed glycosphingolipids in cells. Glucosylceramides are produced by glucosylceramide synthase (GCS) transferring glucose from UDP-glucose to ceramide (Basu, 1968). Recently, it has been shown that human GCS is a glycoprotein containing 394 amino acids encoded from 1,182 nucleotides including a G+C-rich 5' untranslated region of 290 nucleotides (Ichikawa, 1996). Glucosylceramides serve as precursors for the biosynthesis of over 200 known glycosphingolipids. In addition to their role as building blocks of biological membranes, glycosphingolipids have long attracted attention because of their putative involvement in cell proliferation (Hannun and Bell, 1989), differentiation (Schwarz, 1995; Harel and Futerman, 1993), oncogenic transformation (Hakomori, 1981; Morton, 1994) as well as their role in escape from onset of apoptosis (Nakamura, 1996).

Apoptosis or programmed cell death is widely recognized to be a cellular mechanism crucial for toxic response to chemotherapeutic agents (Wyllie, 1997). This process of programmed cell death is involved in a variety of normal and pathogenic biological events and can be induced by a number of unrelated stimuli. Recent studies have implied that a common metabolic pathway leading to cell death may be initiated by a wide variety of signals including hormones, serum growth factor deprivation, chemotherapeutic agents, and ionizing radiation. A substantial body of evidence now exists defining ceramide as a messenger for the induction of apoptosis. In intact cells, rapid ceramide generation is an early event in the apoptotic response to numerous stimuli including cytokines and environmental stresses, and ceramide analogs mimic the effect of stress and induce apoptosis (Hannun, 1994; Kolesnick and Golde, 1994; Hannun and Obeid, 1995; Jarvis, 1996).

It is apparent that agents which affect ceramide metabolism and thus apoptosis have tremendous therapeutic utility for a wide variety of diseases, such as cancer, where regulation of apoptosis and proliferative capacity of tumors are tightly coupled. However, it is particularly difficult to screen for agents based on their apoptotic modulating activity, since such assays require a cell line that can be maintained in vitro and retain sensitivity to apoptosis modulating signals. Additionally, apoptosis endpoint screening assays are cumbersome, time consuming, and at best not reliable due to variability of results.

Various methods exist to test potential therapeutic agents in both the preclinical setting and in clinical trials of individualized patient-specific therapies. These include, among others, the human tumor cloning assay (Shoemaker, 1985), dye exclusion assays (Weisenthal, 1983), adhesive tumor cell culture systems (Ajani, 1987), and multicellular tumor spheroids (Yuhas, 1978). However, most of these are labor intensive when testing for drug sensitivities against single agents, and even more unwieldy when used in evaluating drug combinations. In vivo methods, such as the subrenal capsular assay (Bogden, 1984) and nude mouse tumor culturing (Noso, 1987) offer the obvious benefit of using a system that allows for evaluation of potential host/drug interactions. However, such assays are, by their nature, excessively cumbersome and expensive to use for adequate sampling to fully evaluate either single agents, or combinations of chemotherapeutic drugs (Kratzke and Kramer, 1996).

4. SUMMARY OF THE INVENTION

As shown by the foregoing discussion, it is well established that one of the major factors affecting the clinical outcome of chemotherapy for cancer is the emergence of anticancer drug resistance. The present invention thus addresses the disadvantages of the prior art by providing methods of screening for chemotherapeutic agents, as well as chemosensitizers and uses thereof. Accordingly, it has now been found that the glycolipid metabolic pathway is an attractive target for the identification and design of therapeutically effective chemotherapeutic agents, as well as chemosensitizers, for the treatment of diseases such as cancer. The present invention thus includes screening assays with a biological endpoint, that allow for assessment of the therapeutic potential of a chemotherapeutic agent, using techniques that involve fewer manipulations to allow for the assessment of the therapeutic potential of a chemotherapeutic agent as well as combination therapies (e.g. chemotherapeutic agents and chemosensitizers) and their effective concentrations. The screening assays of the present invention will thus greatly facilitate selection of chemotherapeutic agents or chemosensitizers, or combination therapies for clinical uses (e.g. clinical trials).

One particular aspect of the invention entails a method for assessing the therapeutic potential of a chemotherapeutic agent or chemosensitizer in the treatment of diseases such as cancer, comprising: (i) contacting cells with a chemotherapeutic agent or chemosensitizer, (ii) measuring the level of at least one sphingolipid in the cells, and (iii) comparing the level of the sphingolipid with the level observed in untreated cells. An alteration in the sphingolipid level (in comparison to the sphingolipid level in untreated cells) indicates the therapeutic potential of the chemotherapeutic agent or chemosensitizer, and the dosage range that may be used in in vivo therapy. In a preferred embodiment, the chemotherapeutic agent is to be used in the treatment of cancer. The sphingolipid measured in the method is preferably ceramide or glucosylceramide.

Another aspect of the invention relates to a method of assessing the therapeutic potential of combination therapies which possess synergistic effects leading to superior therapeutic regimens. This method comprises (i) contacting cells with at least one chemotherapeutic agent and at least one chemosensitizer, (ii) measuring the level of at least one sphingolipid in the cells, and (iii) comparing the level of the sphingolipid with the level observed in untreated cells. An alteration in the sphingolipid level is indicative of the synergistic effects of the chemotherapeutic agent and chemosensitizer and a dosage range for the combination that may be used in in vivo therapy. The sphingolipid measured in the method is preferably ceramide or glucosylceramide.

Yet another aspect of the invention is a method of increasing the sensitivity of cancer cells to a chemotherapeutic drug to which cancer cells have acquired resistance by administering one or more chemosensitizers concurrently or sequentially (e.g., before or after the chemotherapeutic agent) with one or more chemotherapeutic agents. The chemosensitizer is administered in an amount effective (i) to allow a reduction in the amount of chemotherapeutic drug while achieving the same degree of effectiveness that was obtained by treatment with the chemotherapeutic drug alone, and (ii) to inhibit the development of MDR in cancer cells.

In yet another aspect of the invention a method for assessing the therapeutic potential of a chemotherapeutic agent in the treatment of diseases such as cancer, comprising: (i) contacting cells expressing glucosylceramide synthase (GCS), preferably over expressing GCS, with at least one chemotherapeutic agent or chemosensitizer, (ii) measuring the activity of GCS in the cells, and (iii) comparing the level of activity of GCS with the level of activity observed in untreated cells. The decrease in the activity of GCS (relative to untreated cells expressing GCS) indicates the therapeutic potential of the chemotherapeutic agent, and the dosage range of the agent to be used in in vivo therapy. In a preferred embodiment, the cells expressing GCS are cancer cells and the activity of GCS is measured by the level of glucosylceramide in the cells.

Another aspect of the invention relates to a method of inducing apoptosis in cells, wherein the method comprises contacting said cells with a chemotherapeutic agent capable of altering the level of at least one sphingolipid (e.g., increasing ceramide or decreasing glucosylceramide) or decreasing the activity of GCS in said cells. The method may further include contacting the cells with a at least one chemosensitizer capable of effecting sphingolipid biosynthesis, preferably by blocking the formation of glucosylceramide from ceramide.

5. BRIEF DESCRIPTION OF THE DRAWINGS

FIG. 1 illustrates the effects of cyclosporines on glucocerebroside (glucosylceramide) levels in MDR breast cancer cells. The glucosylceramide (GC) spot appears as a doublet due to the homogeneity of the aliphatic moieties.

FIG. 2 describes the dose-response effect of cyclosporines on glucocerebroside metabolism in MCF-7-AdrR (adriamycin resistant) cells.

FIG. 3 shows the effect of increasing concentrations of PSC 833 on ceramide and glucosylceramide metabolism in MDR cells.

FIG. 4 describes the temporal profile of the effect of PSC 833 on the metabolism of ceramide and glycosphingolipids.

FIG. 5 describes the effect of PSC 833 on viability of chemosensitive MCF-7 wild type (WT) cells and chemoresistant MCF-7-AdrR cancer cells.

FIG. 6 illustrates the modulation of adriamycin resistance by PSC 833, as shown by lower curve.

FIG. 7 demonstrates the effect of combination chemotherapy on ceramide metabolism in MDR cells (C, control; A, Adriamycin; P, PSC833; T, Tamoxifen, AP, Adriamycin+PSC833; PT, PSC833+Tamoxifen; TA, Tamoxifen+Adriamycin; TAP, Tamoxifen+Adriamycin+PSC833).

FIG. 8 shows the effect of combination chemotherapy on cell viability in an adriamycin-resistant model (C, control; A, Adriamycin; P, PSC833; T, Tamoxifen, AP, Adriamycin+PSC833; PT, PSC833+Tamoxifen; TA, Tamoxifen+Adriamycin; TAP, Tamoxifen+Adriamycin+PSC833).

Figure 1:

FIGS. 12A–12C demonstrates the influence of combination treatment with tamoxifen and ceramide on MDR cells. (A) Analysis of cell viability illustrates that tamoxifen sensitizes MDR cells to ceramide. (B) Photomicrographs of MCF-7 MDR cells after various pharmacologic treatments (upper left, Control; upper right, Tamoxifen; lower left, Ceramide; lower right, Tamoxifen+Ceramide). (C) Gel electrophoreses of cellular DNA (lane 1, Control; lane 2, Tamoxifen; lane 3, Ceramide; lane 4, Tamoxifen+Ceramide; lane 5, standard DNA molecular weight ladder).

Figure 13:
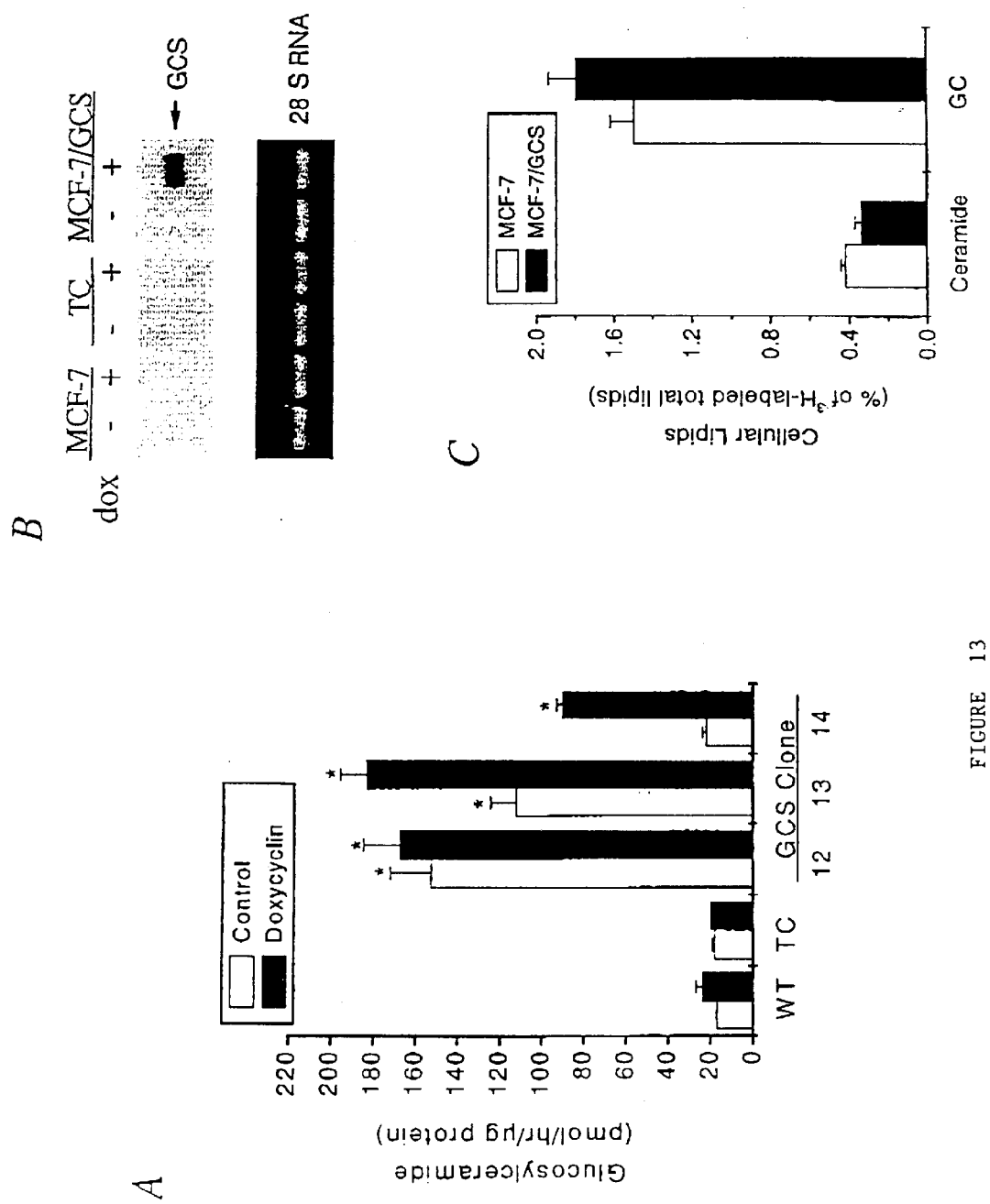

FIGS. 13A–13C shows glucosylceramide synthase (GCS) activity and GCS mRNA expression in MCF-7/GCS cells. Cells were incubated without (−) or with (+) doxycycline (3 µg/ml) for 72 hr. (A) GCS activity of WT, MCF-7 (wild type cells); TC, transfected control cells; $GCS_{12}$, $GCS_{13}$ and $GCS_{14}$, subclones of MCF-7/GCS (glucosylceramide synthase transformed cell line). *p<0.001, compared with MCF-7 cells (subclone $GCS_{14}$ was designated as MCF-7/GCS and used in further experiments). (B) Northern blot analysis of GCS mRNA expression. Dox, doxycycline, TC, transfected control. (C) Ceramide and GC levels in MCF-7/GCS cells in which the lipids were radiolabeled by incubating cells with [$^3$H]palmitic acid.

Figure 14:
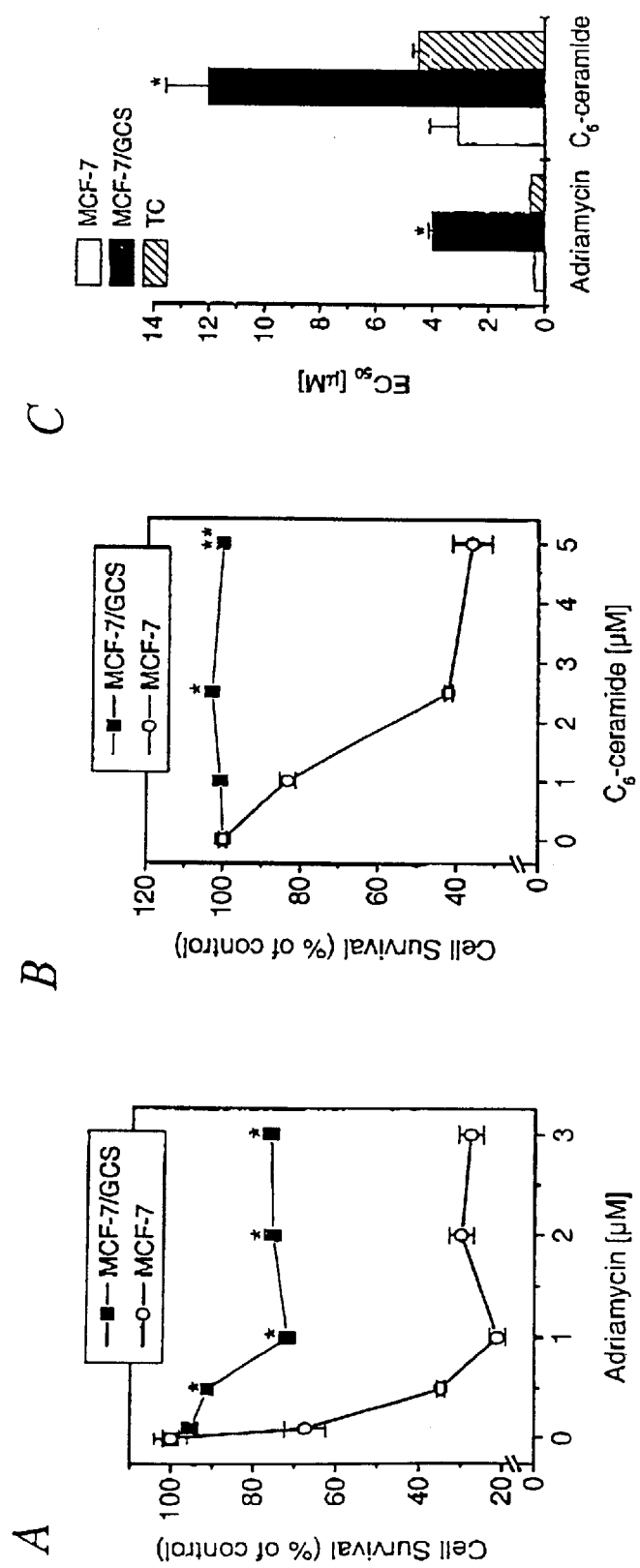

FIGS. 14A–14C shows adriamycin and ceramide toxicity in MCF-7 and in Adriamycin and Ceramide resistance in GCS-transfected MCF-7/GCS cells. (A) Cytotoxicity of adriamycin. The wild type MCF-7 cells were treated without doxycycline and with the adriamycin concentrations shown. Data represent the mean ±SD of six replicates from three independent experiments. *, p<0.001 compared with MCF-7 cells. (B) Cytotoxicity of ceramide. The same conditions cited above were employed, and $C_6$-ceramide was used in place of adriamycin. *, p<0.01, **, p<0.001 compared with MCF-7 cells. (C) $EC_{50}$ of adriamycin and ceramide. * p<0.001 compared with MCF-7 cells.

Figure 15:
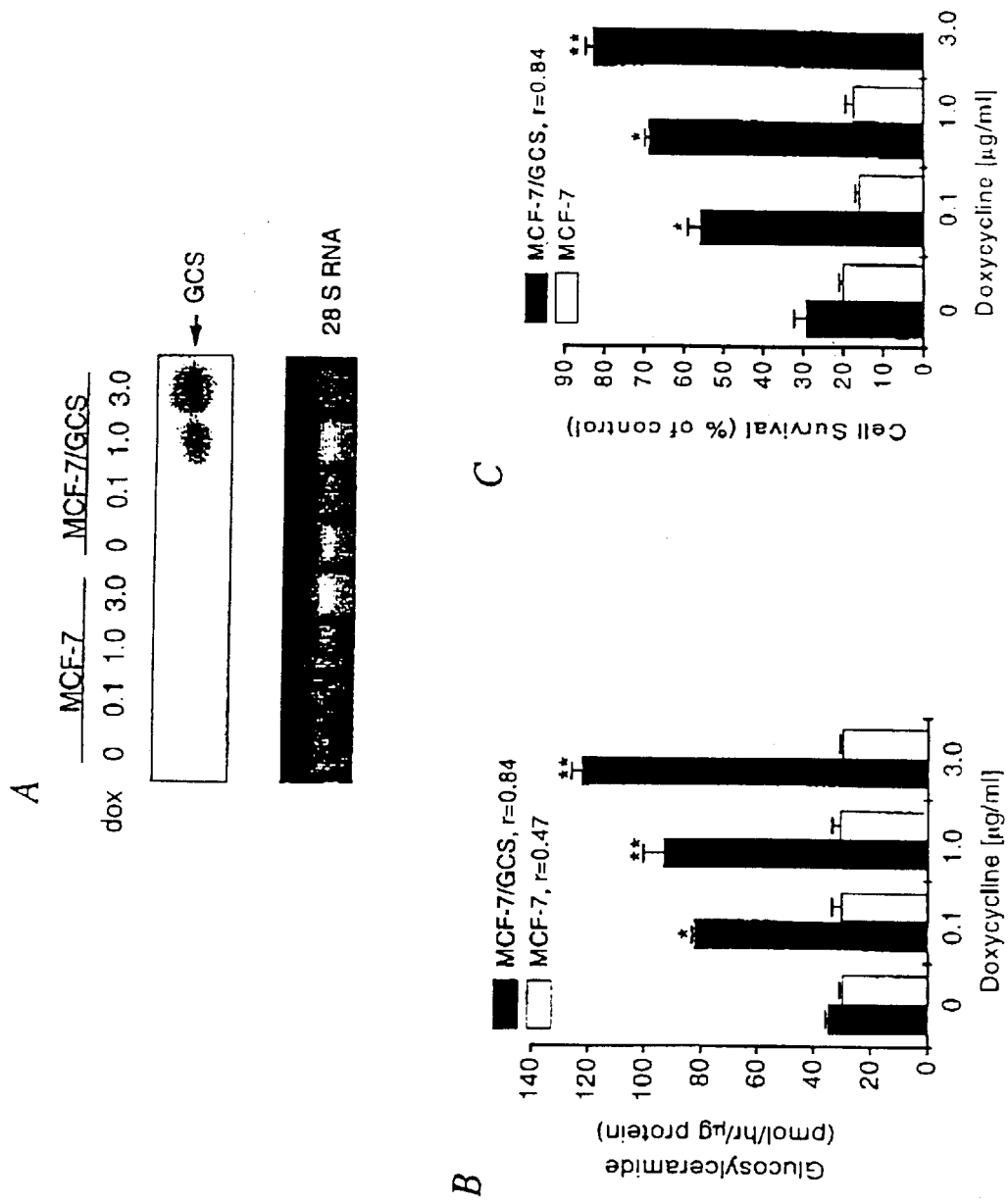

FIGS. 15A–15C shows that doxycycline-induced GCS activity and ceramide resistance coincide with regulated expression of GCS mRNA. (A) Northern Blot showing regulated expression of GCS mRNA in MCF-7 and MCF-7/GCS cells incubated with the indicated concentrations of doxycycline (dox, µg/ml). Total RNA per lane was 15 micrograms. Ethidium bromide-stained RNA (28 S) was used as a control for even loading. Densities of GCS/28 S RNA (×100) in MCF-7/GCS cells were 16, 18, 97, 256 at 0, 0.1, 1.0 and 3.0 µg/ml doxycycline, respectively. (B) Dose-response of GCS activity to doxycycline. Cells were incubated for 96 hr in medium containing the indicated concentrations of doxycycline. GCS activity was analyzed by radioenzymatic assay. * p<0.01, **p<0.001 compared with MCF-7 cells. (C) Doxycycline-induced resistance to ceramide. Cells were pretreated with the indicated concentrations of doxycycline for 48 hr, seeded in 96-well plates, and treated the following day with 5 µM $C_6$ceramide in RPMI-1640 medium containing 5% FBS. Cell viability was determined after 96 hr. Data represent the mean ±SD of six replicates from two independent experiments. Control cells were cultured in medium without $C_6$-ceramide. * p<0.001 compared to MCF-7 cells; **p<0.001, compared to MCF-7 cells exposed to 1.0 µg/ml doxycycline.

Figure 16:
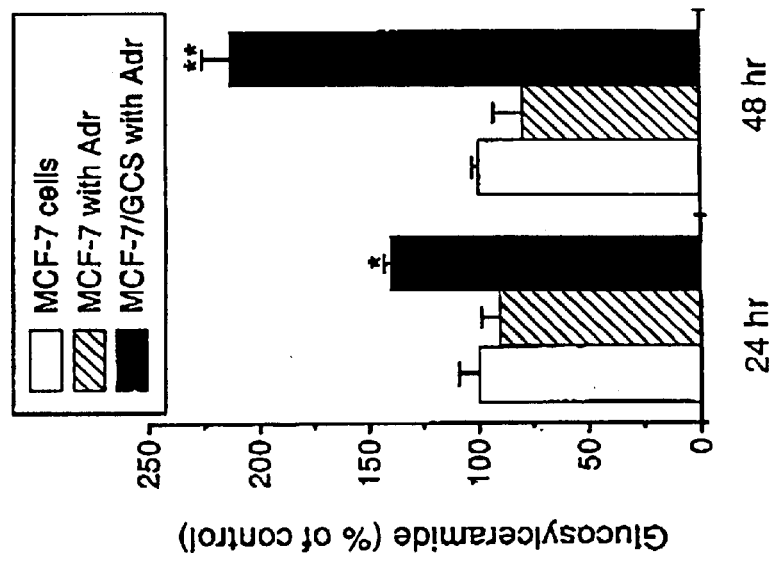
Figure 16:
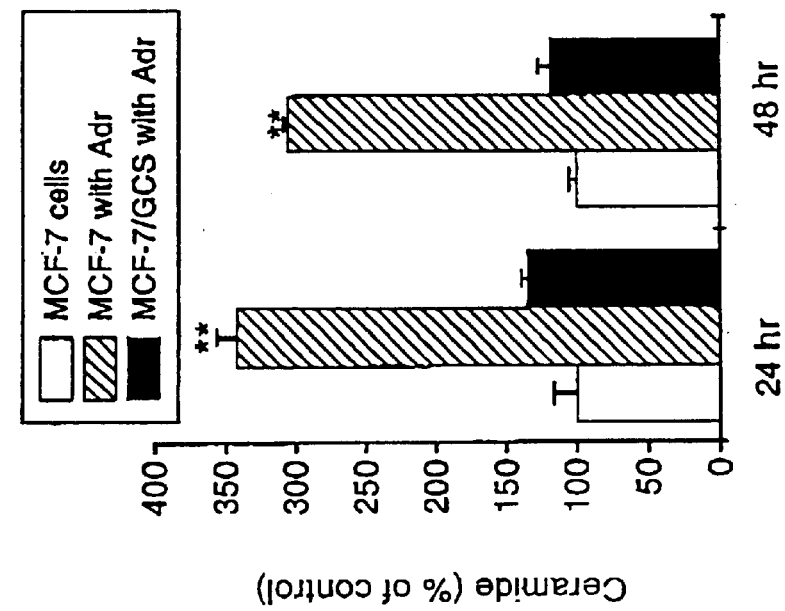

FIGS. 16A–16B shows ceramide metabolism in MCF-7 and in MCF-7/GCS cells in response to treatment with adriamycin. (A) Influence of adriamycin on ceramide metabolism in MCF-7 and in MCF-7/GCS cells. ** p<0.01 compared to MCF-7/GCS cells treated with adriamycin (adr). (B) Influence of adriamycin on GC metabolism in MCF-7 and MCF-7/GCS cells. *p<0.05, **p<0.01 compared to MCF-7 cells treated with adriamycin.

Figure 17:
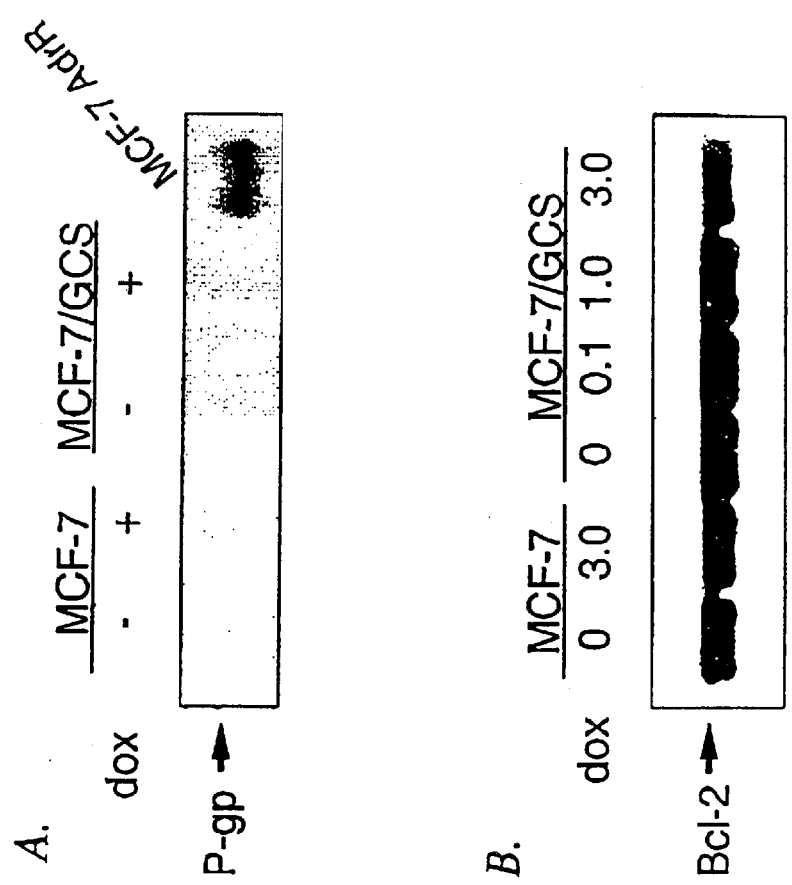

FIGS. 17A-17B shows P-glycoprotein and Bcl-2 expression in MCF-7 and in MCF-7/GCS cells. after cell culture without (−) or with (+) the indicated concentrations of doxycycline. (A) P-glycoprotein (P-gp) Western blot. The immunoblots were incubated with C219, a monoclonal antibody against human P-glycoprotein. When doxycycline (dox) was present, the concentration was 3 µg/ml in the culture medium. MCF-7 AdrR cells (adriamycin resistant) were used as P-glycoprotein positive controls. (B) Bcl-2 Western blot. The immunoblot was incubated with Bcl-2 (Ab-1), a monoclonal antibody against human Bcl-2. The phosphorylated Bcl-2 (top band) and dephosphorylated Bcl-2 (bottom band) localized at ~25 kDa. Doxycycline (dox) was present at the indicated µg/ml amount.

Figure 18:
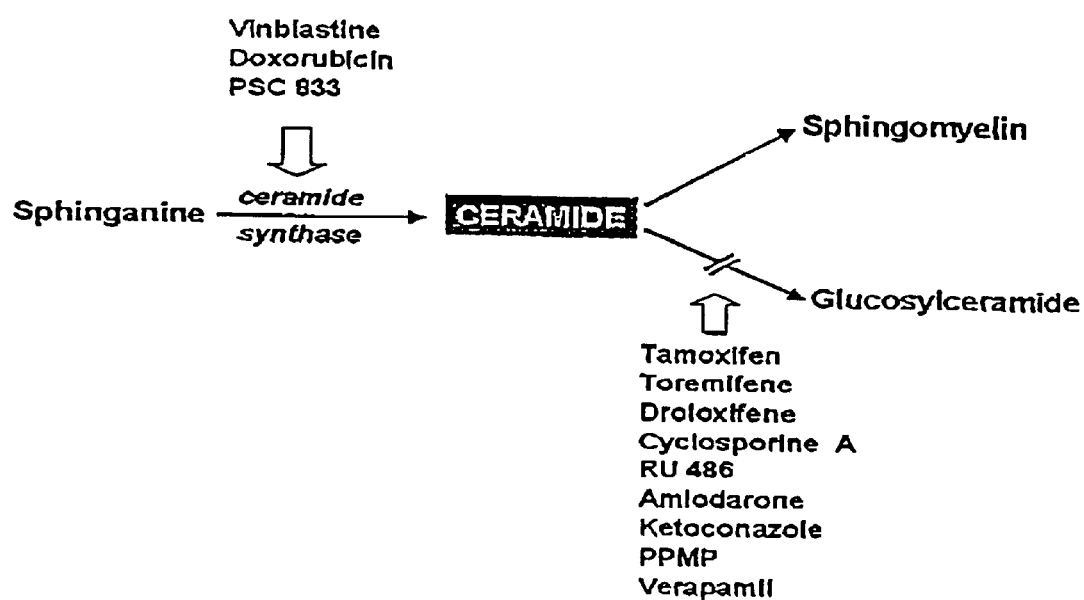

FIG. 18 shows a schematic of the preferred target points in the glycolipid metabolic pathway, specifically the increase in ceramide formation by representative agents shown on the left, and an inhibition in the conversion of ceramide to glucosylceramide by representative agents on the right that block GC formation.

6. DETAILED DESCRIPTION OF THE INVENTION

6.1 Definitions

The term "disease is intended to include, but is not limited to, cancer, autoimmune diseases, or any condition characterized by inappropriate cellular proliferation, such as in diseases of the skin (e.g., psoriasis or hyperkeratosis). Also intended to be included are , viral infection (e.g., HIV), bacterial infection or fungal infection.

The term "cancer" includes, but is not limited to, breast cancer, melanoma, epithelial cell derived cancers, lung cancer, colon cancer, ovarian cancer, breast cancer, kidney cancer, prostate cancer, brain cancer, or sarcomas. Such cancers may be caused by, chromosomal abnormalities, degenerative growth and developmental disorders, mitogenic agents, ultraviolet radiation (UV), viral infections, inappropriate tissue expression of a gene, alterations in expression of a gene, or carcinogenic agents.

The term "sphingolipid" includes any lipid or fatty acid containing sphingosine or sphinganine or 3-keto dihydrosphingosine, as a component. Examples of sphingolipids include, but are not limited to ceramides, glycolipids, and glycosphingolipids.

The term "GCS activity" refers to the biological activities of the naturally occurring GCS enzyme.

By "construct" is meant a recombinant nucleic acid, generally recombinant DNA, that has been generated for the purpose of the expression of a specific nucleotide sequence(s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest.

The term "corresponds to" is meant homologous to or substantially equivalent to or functionally equivalent to the designated sequence.

By "transformation" is meant a permanent or transient genetic change, preferably a permanent genetic change wherein exogenous genetic material is operably inserted and expressed, induced in a cell following incorporation of new DNA (i.e., DNA exogenous to the cell). Where the cell is a mammalian cell (preferably a rodent cell), a permanent genetic change is generally achieved by operative introduction of the DNA into the genome of the cell.

By "cDNA" is meant all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continues open reading frame encoding the protein.

By "genomic sequence" is meant a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

6.2 Methods for Screening Therapeutically Effective Chemotherapeutic Agents by Measuring the Level of a Sphingolipid In accordance with the present invention, it has been discovered that the resistance to chemotherapeutic agents in the treatment of cancer is accompanied by increased cell capacity to metabolize ceramide, via glycosylation, to form glucosylceramide. Increased levels of ceramide, induce an apoptotic response that regulates excessive proliferation of cells. Classical MDR modulators, such as tamoxifen and cyclosporine A, have been found to prevent ceramide glycosylation, and in a doxorubicin-resistant model, sensitivity can be restored by adding tamoxifen to block the glycosylation process. These results demonstrate an important association between the action of MDR modulators and ceramide metabolism, in that cellular resistance to chemotherapeutics is, in some instances, aligned with enhanced cellular ability to eliminate ceramide, a messenger of apoptosis. As such, the glycolipid metabolic pathway is an attractive target for the design of drugs that modulate chemoresistance.

The present invention thus provides methods for assessing the therapeutic potential of a chemotherapeutic agent in treating a disease by assessing the chemotherapeutic agent's ability to modulate glycolipid metabolism. In one embodiment the method assesses the ability of the chemotherapeutic agent to alter the level of at least one sphingolipid in cells. Preferably, this method includes (i) contacting cells with at least chemotherapeutic agent , (ii) measuring the level of at least one sphingolipid, in the cells, and (iii) comparing the level of the sphingolipid with the level observed in untreated cells. An alteration in the sphingolipid level (in comparison to the sphingolipid level in untreated cells) indicates the therapeutic potential of the chemotherapeutic agent, and the dosage range of the agent that may be used in in vivo therapy.

Furthermore, while this method is preferably tailored to the selection of chemotherapeutic agents, the invention also includes methods for identifying chemosensitizers which are able to potentiate or enhance the therapeutic potential of chemotherapeutic agent by modulating glycolipid metabolism. These chemosensitizers distinguish themselves from the classical Pgp MDR modulators by interacting with sphingolipid biosynthesis and/or generation itself, and include agents that block the subsequent glycosylation step of ceramide.

Any sphingolipid may be measured in this method to assess the therapeutic potential of a chemotherapeutic agent or chemosensitizer. By way of example the sphingolipid may be ceramide or glucosylceramide. If the sphingolipid to be measured is ceramide, than an increase in ceramide indicates the therapeutic potential of the chemotherapeutic agent or chemosensitizer. If the sphingolipid to be measured is glucosylceramide, than a decrease in glucosylceramide indicates the therapeutic potential of the chemotherapeutic agent or chemosensitizer. The level of the sphingolipid may be measured by conventional methodology (e.g., Section 6.9). In a preferred embodiment the combination of chemotherapeutic agent and chemosensitizer would increase ceramide levels and block glucosylceramide formation resulting in a synergistic increase in ceramide.

By way of example the method of assessing the therapeutic potential of a chemotherapeutic agent or chemosensitizer in the treatment of diseases such as cancer, may comprise: (i) contacting a cultured cell line, such as the MDR cancer cell line MCF-7 AdrR (Adriamycin resistant) with a chemotherapeutic agent or chemosensitizer, (ii) measuring the level of at least one sphingolipid, such as ceramide or glucosylceramide, in the cultured cells and (iii) comparing the level of the sphingolipid with the level observed in untreated cells. An alteration in the sphingolipid level (in comparison to the sphingolipid level in untreated cells) indicates the therapeutic potential of the chemotherapeutic agent or chemosensitizer, and the dosage range of the agent that may be used in in vivo therapy. If the sphingolipid level measured is that of ceramide, an increase in the level of ceramide indicates the therapeutic potential of the chemotherapeutic agent or chemosensitizer. If the sphingolipid level measured is that of glucosylceramide, a decrease in the level of glucosylceramide indicates the therapeutic potential of the chemotherapeutic agent or chemosensitizer.

6.3 Screening Assay for Effective Combination Therapy

The emergence of drug resistance represents a major obstacle to the successful treatment of cancer with chemotherapy. In an attempt to circumvent the problem of MDR, chemotherapy may utilize combinations of or successive treatments with various chemotherapeutic agents and chemosensitizers to minimize the development of MDR and to reduce the inherent toxicity of chemotherapeutic agents, and at the same time maximize the response to therapy.

Thus, when used in cancer treatment, a chemotherapeutic agent of choice can be administered, irrespective of dosage form and route of administration, in combination with one or more of various other chemotherapeutic agents, as well as potentiating agents, producing a synergistic effect. Thus, a satisfactory therapeutic effect can be observed using chemotherapeutic agents in much lower dosage, thereby minimizing inherent adverse effects.

The present invention provides a method for assessing the therapeutic potential of a wide variety of combination therapies comprised of one or more chemotherapeutic agents and one or more chemosensitizers. In particular, this method entails (i) contacting cells with one or more chemotherapeutic agents, (ii) concurrently or sequentially contacting the cells with one or more chemosensitizers, (iii) measuring the level of at least one sphingolipid, preferably ceramide or glucosylceramide, in the cells, and (iv) comparing the level of the sphingolipid with the level observed in untreated cells. The alteration of the sphingolipid level in the cells contacted with one or more the chemotherapeutic agents and one or more chemosensitizers, indicates the therapeutic potential and a preferred dosage range of the combination.

Any sphingolipid may be measured in the method to assess the therapeutic potential of the combination of one or more chemotherapeutic agents and one or more chemosensitizers. By way of example the sphingolipid may be ceramide or glucosylceramide. If the sphingolipid to be measured is ceramide, than an increase in ceramide indicates the therapeutic potential of the combination. If the sphingolipid to be measured is glucosylceramide, than a decrease in glucosylceramide indicates the therapeutic potential of the combination. The level of the sphingolipid may be measured by conventional methodology (e.g., Section 6.9).

This method is useful in assessing the potentiating effect of a chemosensitizer on a chemotherapeutic agent in the treatment of a disease. Examples of such diseases include but are not limited to, cancer and autoimmune diseases or any disease characterized by inappropriate cell proliferation. These diseases include, but are not limited to, AIDS, AIDS related complex, Karposi sarcoma, leukemia, myelopathy, respiratory disorder such as asthma, autoimmune diseases such as systemic lupus erythematosus, and collagen diseases such as rheumatoid arthritis. In preferred embodiments, the disease is a cancer, as for example, a lymphoma, melanoma, sarcoma, leukemia, retinoblastoma, hepatoma, myeloma, glioma, mesothelioma or carcinoma.

6.4 Method for Screening for Therapeutically Effective Chemotherapeutic Agents by Measuring the Activity of GCS In accordance with the present invention it has been determined that level of GCS activity is increased in cells resistant to chemotherapeutic agents. Accordingly, in yet another aspect of the invention a method for assessing the effectiveness of a chemotherapeutic agent in the treatment of diseases, such as cancer, comprising: (i) contacting cells expressing glucosylceramide synthase (GCS) with a chemotherapeutic agent, (ii) measuring the activity of GCS in the cells, by for example measuring the amount of GC formed, and (iii) comparing the level of activity of GCS with the level of activity observed in untreated cells. The decrease in the activity of GCS (relative to untreated cells expressing GCS) indicates the therapeutic potential of the chemotherapeutic agent, and the dosage range of the agent to be used in in vivo therapy. Alternatively, this method may be used to assess the therapeutic potential of one or chemosensitizers.

Also provided is a method for assessing the therapeutic potential of a wide variety of combinations therapies comprised of one or more chemotherapeutic agents and one or more chemosensitizers, wherein the level of GCS is indicative of the therapeutic potential of the combination. In particular, this method entails (i) contacting cells with one or more chemotherapeutic agents, (ii) concurrently or sequentially contacting the cells with one or more chemosensitizers, (iii) measuring the level of activity of GCS in the cells, and (iv) comparing the level of activity of GCS with the level observed in untreated cells. A decrease in GCS activity in the cells contacted with the one or more chemotherapeutic agent in the presence of one or more chemosensitizers, indicates the therapeutic potential and a preferred dosage range for the combination of chemotherapeutic agent and chemosensitizer.

In a preferred embodiment the cells expressing the GCS, are cancer cells. The activity of GCS may be measured by conventional methodologies known to those skilled in the art (See, for e.g., Section 6.10). By way of example, GCS activity may be measured by formation of glucosylceramide formation

6.5 Method for Inducing Apoptosis in Cells

In accordance with the present invention it has been determined that increase in ceramide levels in cells, preferably accompanied by a decrease in glucosylceramide formation induces apoptosis in cells. Accordingly, yet another aspect of the invention relates to a method of inducing apoptosis in cells, wherein the method comprises contacting said cells with a chemotherapeutic agent capable of altering the level of at least one sphingolipid (e.g., increasing ceramide or decreasing glucosylceramide) or decreasing the activity of GCS in said cells. The method may further include contacting the cells with a at least one chemosensitizer capable of effecting sphingolipid biosynthesis, preferably by blocking the formation of glucosylceramide from ceramide. The cells may be any type of cell, in a preferred embodiment the cells are cancer cells.

6.6 Cells.

A variety of cells may be used in the methods of the subject application. Preferably, the cells to be used in the disclosed methods exhibit inappropriate cellular proliferation, such as, cancer cells. Nonlimiting examples of cancer cells that may be used include, but are not limited to, breast, lymphoma, melanoma, sarcoma, leukemia, retinoblastoma, hepatoma, myeloma, glioma, mesothelioma or carcinoma cells. By way of example, the cells used in the methods may be primary cultures (e.g., developed from biopsy or necropsy specimens) or cultured cell lines. Methods of maintaining primary cell cultures or cultured cell lines are well known to those of skill in the art.

If cultured cell lines are used, preferably the cell lines are mammalian cancer cells, most preferably human cancer cells. Examples of cell lines that may be used include, but are not limited to MCF-7 (a breast cancer cell line), MCF-7 AdrR (adriamycin resistant), OVCAR-3 (human ovarian cancer cell line), melanoma cell lines (e.g., M-10, M-24, M-101; John Wayne Cancer Institute, Santa Monica, Calif., U.S.A.) and MCF-7/GCS (e.g., Examples 8–11) Desirable cell lines are often commercially available (e.g. American Type Culture Collection, 10801 University Blvd., Manassas Va., 20110–2209), available from the National Cancer Institute (Rockville, Md., U.S.A.)or readily made by conventional technology. By way of example, MDR cell lines may be produced by continues exposure of cells to chemotherapeutic agents followed by cloning of the resistant cells.

Cells of any type which express GCS may be used in the methods measuring GCS activity. The cells may be naturally occurring or produced by conventional technology. By way of example, if the cells are naturally occurring they may express GCS at normal levels for that particular cell type or they may be naturally occurring cells expressing increased levels of GCS. Examples of such cells include, but are not limited to, MCF-7AdrR cells, or melanoma cell lines (e.g., M-10, M-24, M-101; John Wayne Cancer Institute, Santa Monica, Calif., U.S.A.). Desirable cell lines are often commercially available (e.g. American Type Culture Collection, 10801 University Blvd., Manassas Va., 20110–2209), available from the National Cancer Institute (Rockville, Md., U.S.A.)or readily made by conventional technology.

Alternatively, cells may be transformed with a construct comprising nucleic acid sequences encoding GCS to produce cells expressing GCS. Examples of such cells include but are not limited to MCF-7/GCS (e.g., Examples 8–11). The nucleic acid sequences encoding the GCS may be cDNA or genomic DNA or a fragment thereof. Sequences for GCS are known in the art. Examples of GCS sequences include, but are not limited to, Ickikawa et al., 1996. The nucleic acid sequences used to produce the GCS expressing cells of the subject invention may encode all or a part of the GCS protein as appropriate. Preferably the coding sequence for GCS or regions sufficient to effect GCS activity.

Portions of fragments of the coding sequence for GCS may be obtained by chemically synthesizing oligonucleotides in accordance with conventional methods, by restriction enzyme digestion, by PCR amplification, etc. The introduced coding sequence or parts thereof may be derived from a wild-type genes, naturally occurring polymorphisms, or a genetically manipulated sequences (i.e., deletions, substitutions or insertions in the coding or non-coding regions) or sequences encoding a truncated or altered GCS.

Vectors suitable for use in expressing GCS comprise at least one expression control element operably linked to the nucleic acid sequence encoding GCS. Expression control elements are inserted in the vector to control and regulate the expression of the nucleic acid sequence. Examples of expression control elements include, but are not limited to, lac system, operator and promoter regions of phase lamda, yeast promoters, and promoters derived from polyoma, adenovirus, retroviruses, or SV40. It will be understood by one skilled in the art the correct combination of required or preferred expression control elements will depend on the cells to be used.

The nucleic acid sequence encoding all or fragments thereof of the GCS may be introduced into an appropriate vector for extrachromosomal maintenance or for integration into the host. Preferably a vector that allows for stable integration into the genome is used. Examples of such vectors, but are not limited to retroviral vectors, vaccinia virus vectors, adenovirus vectors, herpes virus vector, fowl pox virus vector, plasmids, YACs, or Tet on gene expression vector from Clontech (Palo Alto, Calif.).

The vector may further comprise additional operational elements including, but not limited to, leader sequences, termination codons, polyadenylation signals, and any other sequences necessary or preferred for the appropriate transcription and/or translation of the nucleic acid sequence encoding GCS.

It will be further understood by one skilled in the art that such vectors are constructed using conventional methodology (See e.g. Sambrook et al., (eds.) (1989) "Molecular Cloning, A laboratory Manual" Cold Spring Harbor Press, Plainview, New York; Ausubel et al., (eds.) (1987) "Current Protocols in Molecular Biology" John Wiley and Sons, New York, N.Y.) or are commercially available.

It may be preferable to express GCS in cells that mimic the native pattern of expression in humans. A specific expression pattern may be accomplished by placing the nucleic acid encoding the GCS or under the control of an inducible or developmentally regulated promoter, or under the control of a tissue specific or cell type specific promoter. By way of example, specific expression patterns may be accomplished by the use of genomic sequences for GCS.

The means by which the cells may be transformed with the construct comprising the nucleic acid sequences encoding all or part of GCS includes, but is not limited to, microinjection, electroporation, transduction, transfection, lipofection calcium phosphate particle bombardment mediated gene transfer or direct injection of nucleic acid sequences or other procedures known to one skilled in the art (Sambrook et al. (1989) in "Molecular Cloning. A Laboratory Manual", Cold Spring Harbor Press, Plainview, N.Y.). For various techniques for transforming mammalian cells, see Keown et al. 1990 Methods in Enzymology 185:527–537.

The cells to be transformed with a GCS construct preferably in cells exhibiting inappropriate cellular proliferation, such as, cancer cells. Nonlimiting examples of cancer cells that may be used include, but are not limited to, breast cancer, lymphoma, melanoma, sarcoma, leukemia, retinoblastoma, hepatoma, myeloma, glioma, mesothelioma or carcinoma cells. By way of example, the cells used in the methods may be primary cultures (e.g., developed from biopsy or necropsy specimens) or cultured cell lines. Methods of maintaining primary cell cultures or cultured cell lines are well known to those of skill in the art.

If cultured cell lines are used, preferably the cell lines are mammalian cancer cells, most preferably human cancer cells. Examples of cell lines that may be used include, but are not limited to. MCF-7 (a breast cancer cell line) transformed with a GCS constuct. Such continues cell lines are often commercially available (e.g. American Type Culture Collection, 10801 University Blvd., Manassas Va., 20110–209) or readily made by conventional technology.

6.7 Chemotherapeutic Agents and Chemosensitizers

Candidate chemotherapeutic agents suitable for assaying in the methods of the subject application may be any type of molecule from, for example, chemical, nutritional or biological sources. The chemotherapeutic agent may be a naturally occurring or synthetically produced. For example, the chemotherapeutic agent may encompass numerous chemical classes, though typically they are organic molecule, preferably small organic compounds having a molecular weight of more than 50 and less than about 2,500 Daltons. Such molecules may comprise functional groups necessary for structural interaction with proteins or nucleic acids. By way of example, chemical agents may be novel, untested chemicals, agonists, antagonists, or modifications of known therapeutic agents.

The chemotherapeutic agents may also be found among biomolecules including, but not limited to, peptides, saccharides, fatty acids, antibodies, steroids, purines, pryimidines, toxins conjugated cytokines, derivatives or structural analogs thereof or a molecule manufactured to mimic the effect of a biological response modifier. Examples of chemotherapeutic agents from nutritional sources include, but is not limited to, extracts from plant or animal sources or extracts thereof.

Chemotherapeutic agents may be obtained from a wide variety of sources including libraries of synthetic or natural compounds. Alternatively, libraries of natural compounds in the form of bacterial, fungal, plant, and animal extracts are available or readily produced, natural or synthetically produced libraries or compounds are readily modified through conventional chemical, physical and biochemical means, and may be used to produce combinatorial libraries. Known pharmacological agents may be subjected to random or directed chemical modifications, such as acylation, alkylation, esterification, amidification, etc. to produce structural analogs.

Chemotherapeutic agents may prevent initiation of a disease or attenuate or alleviate the symptoms of the disease. By way of example, for cancer, chemotherapeutic agents may prevent initiation of malignant cells or arrest or reverse the progression of premalignant cells to malignant disease or the chemotherapeutic agents may serve to attenuate or alleviate a cancer. In a preferred embodiment, the screening of the chemotherapeutic agents is performed on cancer cells.

Chemosensitizers are molecules that potentiate or enhance the activity of a chemotherapeutic agent, preferably by causing a synergistic effect. Chemosensitizers generally work by allowing a lower dosage of the chemotherapeutic agent to be used thereby minimizing inherent adverse effects or by inhibiting MDR by modulation of the resistance biology. Chemosensitizers generally act via Pgp, glutathione-S-transferase, topoisomerases, and other proteins associated with MDR. In accordance with the present invention, however, it has been discovered that resistance to chemotherapeutic agents is accompanied by an increase in the capacity of the cells to metabolize ceramide, via glycosylation, to form glucosylceramide and that inhibition of this metabolic pathway restores sensitivity of the cells to the chemotherapeutic agent. Preferably the chemosensitizers of the subject invention modulate sphingolipid metabolism, such as for example, by inhibiting the conversion of ceramide to glucosylceramide and/or by increasing ceramide generation.

Some chemosensitizers may also be chemotherapeutic agents as well, for example, tamoxifen Chemosensitizers suitable for use may be any type of molecule from, for example, chemical, nutritional or biological sources. Thus chemosensitizers for screening in the subject invention may be obtained from the same type of molecules or compounds described herein and above for chemotherapeutic agents.

6.8 Diseases

This methods of the subject invention are useful in identifying chemotherapeutic agents that are capable of modulating glycolipid metabolism and thus regulating apoptosis. Accordingly, this method is useful for evaluating the therapeutic potential of a chemotherapeutic agent for treating diseases. Examples of such diseases include, but is not limited to cancer and autoimmune diseases that are characterized by inappropriate cell proliferation. These diseases include, but are not limited to, AIDS, AIDS related complex, Karposi sarcoma, leukemia, myelopathy, respiratory disorder such as asthma, autoimmune diseases such as systemic lupus erythematosus, and collagen diseases such as rheumatoid arthritis. In preferred embodiments, the disease is a cancer, as for example, a lymphoma, melanoma, sarcoma, leukemia, retinoblastoma, hepatoma, myeloma, glioma, mesothelioma or carcinoma.

6.9 Methods of Detection of the Sphingolipid

The present invention encompasses methods for determining the therapeutic potential of a chemotherapeutic agent by measuring the sphingolipid level of cells contacted with the chemotherapeutic agent and comparing the level with the levels observed in untreated cells of the same type. The method of measuring may, for example, comprise chromatographic separation of the lipid components of the cell, and the chromatographic separation may comprise, for example, thin layer chromatography, gas chromatography, high performance liquid chromatography, paper chromatography, affinity chromatography or supercritical flow chromatography.

The method of measuring also may comprise contacting the components of said cell with a first antibody that binds to an epitope on the sphingolipid. This particular method may also comprise contacting the antibody component mixture with a second antibody that binds to said first antibody, and is labelled in a manner that facilitates its detection.

6.9.1. Chromatographic Methods of Detection.

Typically, the lipid components of a cell will be radiolabeled by incubation of the cell with [$^3$H]carbon-containing molecules that are direct or indirect precursors in lipid biosynthesis. Separation of labeled lipid components from (i) non-lipid components and (ii) each other permits quantitation of the different lipid species. Quantitation of separated components may be achieved by any standard methodology, but would include photodensitometric scanning of thin-layer chromatography plates if $^3$H is not used or scintillation counting of lipid samples separated by various chromatographic techniques.

Any of a wide variety of chromatographic procedures may be employed. For example, thin layer chromatography, gas chromatography, high performance liquid chromatography, paper chromatography, affinity chromatography or supercritical flow chromatography may be employed (Katz, 1987; Katz, 1996).

Partition chromatography is based on the theory that if two phases are in contact with one another, and if one or both phases constitute a solute, the solute will distribute itself between the two phases. Usually, partition chromatography employs a column which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatography well known in the art, are paper chromatography and thin-layer chromatography (TLC) (Touchstone, 1992). Both of these techniques are also referred to as adsorption chromatography. Other examples of partition chromatography are gas-liquid and gel chromatography. TLC systems useful to separate glucosylceramides and ceramides are describes in, for example, Cabot et al., 1997, Lavie, 1996 and Lavie 1997.

Gas-Liquid chromatography (GLC) is a technique well known in the art to separate small molecules. In GLC, the mobile phase is a gas and the stationary phase is a liquid adsorbed either to the inner surface of a tube or column or to a solid support. The liquid usually is applied as a solid dissolved in a volatile solvent such as ether. The sample, which may be any substance that can be volatilized, is introduced as a liquid with an inert gas, such as helium, argon or nitrogen, and then heated. The vaporized compounds continually redistribute themselves between the gaseous mobile phase and the liquid stationary phase, according to their partition coefficients (Grob, 1995).

Gel chromatography, or molecular sieve chromatography, is a special type of partition chromatography that is based on molecular size. The pore size of the column material, e.g. dextran, agarose, polyacrylamide, allows the separation of large molecules from smaller molecules as they pass through or around the pores independent of other factors such as pH, ionic strength, temperature, etc. There also is virtually no adsorption, less zone spreading and simple derivation of the molecular weight from the elution volume (Yau, 1979).

High Performance Liquid Chromatography (HPLC) is characterized by a very rapid separation with extraordinary resolution of peaks using only small amounts of a sample. This is achieved by the use of very fine particles and high pressure to maintain an adequate flow rate (Patonay, 1992; Katz, 1996; Snyder, 1997).

Affinity Chromatography is a chromatographic procedure that relies on a receptor-ligand interaction, i.e. on a specific affinity between a ligand to be isolated and a molecule, e.g. a receptor, to which it specifically binds. The column material is synthesized by covalently coupling one of the binding partners, e.g. the receptor, to an insoluble matrix without affecting the ligand binding site. The column material is then able to specifically adsorb the ligand from the solution. Elution occurs by changing the conditions to disrupt binding (e.g., pH, ionic strength, temperature, etc.). The matrix should be a substance that itself does not adsorb molecules to any significant extent and that has a broad range of chemical, physical and thermal stability.

6.9.2. Monoclonal Antibody Production and Methods of Detection Using Antibodies In general, techniques for preparing polyclonal and monoclonal antibodies as well as hybridomas capable of producing the desired antibody are well known in the art (Campbell, 1984; Kohler and Milstein, 1975). These include, e.g., the trioma technique and the human B-cell hybridoma technique (Kozbor, 1983; Cole, 1985).

Any animal (mouse, rabbit, etc.) that is known to produce antibodies can be immunized with the immunogenic composition. Methods for immunization are well known in the art and include subcutaneous or intraperitoneal injection of the immunogen. One skilled in the art will recognize that the amount used for immunization will vary based on the animal which is immunized, the antigenicity of the immunogen, and the site of injection.

The immunogen may be modified or administered in an adjuvant to increase its antigenicity. Methods of increasing antigenicity are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify hybridoma cells that produce an antibody with the desired characteristics. These include screening the hybridomas with an enzyme-linked immunosorbent assay (ELISA), western blot analysis, or radioimmunoassay (RIA) (Lutz, 1988). Hybridomas secreting the desired antibodies are cloned and the immunoglobulin class and subclass may be determined using procedures known in the art (Campbell, 1984).

Techniques described for the production of single chain antibodies (U.S. Pat. No. 4,946,778) can be adapted to produce single chain antibodies to the sphingolipids of the present invention.

For polyclonal antibodies, antibody containing antisera is isolated from the immunized animal and is screened for the presence of antibodies with the desired specificity using one of the above-described procedures.

In the present invention, the above-described antibodies are used in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as fluorescein or rhodamine, etc.), paramagnetic atoms, etc. Procedures for accomplishing such labeling are well-known in the art, for example, see Sternberger, 1970; Bayer, 1979; Engval, 1972; Goding, 1976. The labeled antibodies of the present invention can then be used for in vitro, in vivo, and in situ assays to identify the sphingolipid (or a fragment thereof) in various cells or tissues. Preferred immunoassays are the various types of ELISAs and RIAs known in the art. The antibodies themselves may also be used directly in therapies or other diagnostics.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, 1986; Jacoby, 1974). The immobilized antibodies of the present invention can be used for in vitro, in vivo, and in situ assays as well as for immuno-affinity purification of the sphingolipids.

6.10 Methods of Measuring GCS Activity

The present invention encompasses methods for determining the therapeutic potential of a chemotherapeutic agent by measuring the activity of GCS in cells contacted with the chemotherapeutic agent and comparing the level with the levels observed in untreated cells of the same type. The activity of GCS may be measured by conventional methods known to those skilled in the art. For example, GCS activity may be measured by the incorporation of tritium in cultured cells. The cultured cells are incubated with a tritiated precursor, such as [$^3$H] palmitic acid and then contacted with one or more chemotherapeutic agents or one or more chemosensitizers or combinations thereof. The lipids of the cultured cells are seperated by TLC. The activity of GCS is assessed by measuring the amount of tritium in glucosylceramide relative to tritium in other lipids (e.g., Cabot, 1997; Lavie, 1996, Lavie 1997) and compared to the activity of GCS in untreated cells. Alternatively, the level of ceramide may be measured to determine the therapeutic potential. By way of example, cultured cells are incubated with a tritiated precursor, such as [$^3$H] palmitic acid and then contacted with one or more chemotherapeutic agents or one or more chemosensitizers or combinations thereof. TLC using a solvent system containing chloroform/acetic acid (90:10, v/v) may be used to resolve lipids from lipid extracts of the cell, and the amount of labeled ceramide assessed by comparison with untreated cells. Yet another method of measuring ceramide to determine GCS activity uses a commercial kit to measure the [$^{32}$P]-ATP phosphorylation of ceramide.

Examples of additional methods include analysis of the level of expression of the GCS mRNA or protein. The GCS protein may be detected by methods known in the art which include, for example, Coomassie blue staining, silver staining and Western blotting using antibodies specific for the GCS protein. Alternatively the GCS expressed by the cells may be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for GCS. (Ausubel et. al., (1987) in "Current Protocols in Molecular Biology" John Wiley and Sons, New York, N.Y.).

Another method for assessing GCS activity relates to assays detecting messenger RNA or DNA encoding GCS. RNA can be isolated as whole cell RNA or as poly(A) sup+RNA. Whole cell RNA and polyA RNA can be isolated by a variety of methods known to those skilled in the art. (Ausubel et al., (1987) on "Current Protocols in Molecular Biology", John Wiley and Sons, New York). Standard methods for isolating DNA from a biological sample, detecting alterations in a gene and detecting complex between the nucleic acid probe and genomic DNA sequences are provided in manuals such as Sambrook et al., (eds) (1989) "Molecular Cloning, A Laboratory Manual", Cold Spring Harbor Press, Plainview, N.Y. and in Ausubel et al., (eds) (1987) in "Current Protocols in Molecular Biology" John Wiley and Sons, New York, N.Y. Conventional Methodology may be used to resolve and detect the mRNA or DNA (Sambrook et. al., (1989) in "Molecular Cloning, A Laboratory Manual", Cold Spring Harbor Press, Plainview, N.Y.; Ausubel et al., (1987) in "Current Protocols in Molecular Biology, John Wiley and Sons, New York, N.Y.). Standard techniques may be used to label the probes of this invention. Sambrook et al., (eds) (1989) "Molecular Cloning, A Laboratory Manual", Cold Spring Harbor Press, Plainview, N.Y. and in Ausubel et al., (eds) (1987) in "Current Protocols in Molecular Biology" John Wiley and Sons, New York, N.Y. Radioactive and non-radioactive labelling kits are also commercially available.

6.11 Diagnostic Kits

All the essential materials and reagents required for determining sphingolipid levels or GCS activity in a sample, or for inducing apoptosis in cells, or for inhibiting inappropriate cellular proliferation, such as tumor cell proliferation, may be assembled in a kit. When the components of the kit are provided in one or more liquid solutions, the liquid solution preferably is an aqueous solution, with a sterile, aqueous solution being particularly preferred.

For the detection of sphingolipids, the kit may contain materials for chromatographic separation, such as columns, beads, resins, gel matrices, filters, TLC plates, buffers and appropriate solvents. Alternatively, if the detection is via immunologic means, the kit may contain antibodies directed to the sphingolipids, secondary antibodies that bind primary antibodies, labels or signal generating compounds (either conjugated or unconjugated) and various reagents for the generation and detection of signals. The kit may also contain nucleic acid sequences to be used as probes in, for example PCR or Northern Blot Analysis.

For in vivo use, a chemotherapeutic agent either alone or in combination with, a chemosensitizer, preferably one that inhibits formation of glucosylceramide from ceramide may be formulated into single or separate pharmaceutically acceptable compositions. In this case, the container means may itself be an inhalant, syringe, pipette, eye dropper, or other like apparatus, from which the formulation may be applied to an infected area of the body, such as the lungs, injected into an animal, or even applied to and mixed with the other components of the kit.

The components of these kits may also be provided in dried or lyophilized forms. When reagents or components are provided as a dried form, reconstitution generally is by the addition of a suitable solvent, which may also be provided in another container means. The kits of the invention may also include an instruction sheet defining administration of the chemotherapeutic agent and/or chemosensitizer to modulate glycolipid metabolism. or explaining the assays for determining sphingolipid levels in samples. The kits of the present invention also will typically include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

6.12 Pharmaceutical Compositions and Routes of Administration

Aqueous compositions of the present invention are comprised of an effective amount of the chemotherapeutic agent, either alone or in combination with another agent (for example, but not limited to a chemotherapeutic agent alone or in combination with a chemosensitizer.) Such compositions will generally be dissolved or dispersed in a pharmaceutically acceptable carrier or aqueous medium. The terms "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying, agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other chemotherapeutic agents or classical MDR modulators, can also be incorporated into the compositions.

The active compounds of the present invention can be formulated for parenteral administration, e.g., for injection via the intravenous, intramuscular, sub-cutaneous, or intraperitoneal routes. The preparation of an aqueous composition that contains a chemotherapeutic agent alone or in combination with a chemosensitizer as active ingredients will be known to those of skill in the art in light of the present disclosure. Typically, such compositions can be prepared as injectables, such as liquid solutions or suspensions. Solid forms, that can be formulated into solutions or suspensions upon the addition of a liquid prior to injection, as well as emulsions, can also be prepared.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof, as well as in oils. Under ordinary conditions of storage and use, these preparations contain a preservative to prevent the growth of microorganisms.

The pharmaceutical forms suitable for injectable use include (i) sterile aqueous solutions or dispersions, (ii) formulations including sesame oil, peanut oil or aqueous propylene glycol, and (iii) sterile powders for the extemporaneous preparation of sterile injectable solutions or dispersions. In all cases the form must be sterile and must be fluid to allow for easy use with a syringe. It must be stable under the conditions of manufacture and storage, and must be preserved against the contaminating action of microorganisms, such as bacteria and fungi.

The active compounds may be formulated into a composition in a neutral or salt form. Pharmaceutically acceptable salts include inorganic acids, e.g. hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents. Prolonged absorption of the injectable compositions can be brought about by including in the compositions agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in a therapeutically effective amount. The formulations are easily administered in a variety of dosage forms, such as the type of injectable solutions described above, with even drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure Some variation in dosage will necessarily occur depending on the condition of the subject being treated. The person responsible for administration will, in any event, determine the appropriate dose for the individual subject. Veterinary uses are also intended to be encompassed by this invention.

All books, articles, or patents referenced herein are incorporated by reference. The following examples illustrate various aspects of the invention, but in no way are intended to limit the scope thereof.

6.13 EXAMPLES

6.13.1. Methods

6.13.1a. Methods for Examples 1–7

Cells. Experiments were conducted using the human MDR breast cancer cell line, MCF-7 AdrR (adriamycin resistant) provided by Drs. Kenneth H. Cowan and Merrill E. Goldsmith, National Cancer Institute. Cells were grown in RPMI-1640 medium containing 10% FBS (fetal bovine serum) and antibiotics as previously described (Lavie, 1997) and cultures were maintained in a humidified 6.5% $CO_2$ atmosphere incubator. Trypsin (0.05%) and EDTA (0.5 mM) were used for subculture. Plastic tissue cultureware, was from Costar (96-well plates) and Corning (6-well plates, 6-cm dishes, T-75 flasks). Limited experiments were conducted using the human MDR epidermoid carcinoma cell line, KBV-1, provided by Dr. Michael M. Gottesman, National Cancer Institute. Cells were maintained as described (Lavie, 1996). Vinblastine was eliminated from the culture medium during the experiments.

Cell Radiolabeling and Lipid/Glycolipid Analysis. To follow lipid metabolism, cells were grown in the presence of tritiated ceramide precursors, L-[$^3$H]serine (20 Ci/mmol) (American Radiolabeled Chemicals, Inc., St. Louis), and [9, 10-$^3$H]palmitic acid (50 Ci/mmol) (DuPont NEN). Labeling media were prepared by adding microliter amounts of tritiated compounds (supplied in ethanol or sterile water) to medium containing only 5% FBS. After radiolabeling, 0.1 ml aliquots of medium were removed and analyzed by LSC (Lavie, 1997), in order to determine cellular uptake of the tritiated compounds. Cell monolayers were then rinsed twice with cold phosphate-buffered saline. Ice cold methanol containing 2% acetic acid was added, and cells were scraped free of the substratum (plastic scraper) for lipid extraction using chloroform and water in 1-dram glass vials as described (Lavie, 1997; Lavie, 1996; Bligh and Dyer, 1959). After centrifugation, the resulting organic lower phase of the biphasic extraction was withdrawn, transferred to a glass vial, and evaporated to dryness under a stream of nitrogen.

Radioactivity in glucosylceramide was analyzed by TLC resolution of total lipids (Silica Gel G) using a solvent system containing chloroform/methanol/ammonium hydroxide (80:20:2, v/v/v). Migration of glucosylceramide on TLC was compared with that of commercial standard (glucocerebrosides, Gaucher's spleen, Matreya, Inc., Pleasant Gap, Pa.), and lipid spots, after iodine vapor visualization, were scraped for tritium quantitation by LSC (Lavie, 1997; Lavie, 1996). [$^3$H]Ceramide was resolved from other labeled lipids by TLC using a solvent system containing chloroform/acetic acid (90:10, v/v), and [$^3$H] sphingomyelin was resolved by TLC in chloroform/methanol/acetic acid/water (60:30:7:3 v/v/v/v). Ceramide and sphingomyelin commercial standards (brain-derived) were from Avanti Polar Lipids, Alabaster, Ala. After iodine visualization of lipids, areas of the chromatogram corresponding to ceramide and sphingomyelin were scraped into minivials containing 0.5 ml water followed by 4.5 ml EcoLume (ICN, Costa Mesa, Calif.), and samples were analyzed for tritium by liquid scintillation spectrometry. Alternative analysis of ceramide consisted of subjecting an aliquot of the total cell lipid extract to mild alkaline hydrolysis (0.1 N KOH in methanol, 1 h at 37° C.) followed by re-extraction (Lavie, 1997). Ceramide was then resolved by TLC in a solvent system containing hexane/diethyl ether/formic acid (60:40:1, v/v/v). Both methods of ceramide analysis yielded similar results. The same can also be done without tritium by simply applying 100–200 µg total cell lipid to TLC plates and developing them in the appropriate solvent, then spraying them with 30% $H_2SO_4$, charring the plate in an oven at 180° C. for 20 min, and measuring lipid mass by densitometry.

Cytotoxicity Assays. MCF-7-AdrR cells, counted by hemocytometer, were seeded into 96-well plates (2,000–2,500 cells/well) in 0.1 ml RPMI-1640 medium containing 5% FBS. Cells were incubated for 24 h before addition of drugs. Perimeter wells of the 96-well plates for cells contained 0.2 ml water and were not used. Drugs were dissolved in the appropriate vehicles (see below), diluted into 5% FBS-containing medium and added to each well in a final volume of 0.1 ml. Cells were incubated at 37° C. for the times indicated. The cytotoxic activity of a drug was determined using the Promega Cell Titer 96™ Aqueous cell proliferation assay kit. Each experimental point was performed in six replicates. Promega solution (20 µl, not the suggested 40 µl) was aliquoted to each well, and cells were place at 37° C. for 2–3 h or until an optical density of 0.9–1.2 was obtained as the highest reading. Absorbence at 490 nm was recorded using an enzyme-linked immunosorbent assay plate reader (Molecular Devices, San Diego, Calif.).

Drugs and Vehicles. Adriamycin (Sigma) was prepared in sterile water at a final concentration of 1.0 mM. Tamoxifen, free base (Sigma) was prepared as a 20 mM stock solution in acetone. SDZ PSC 833 ([3'-Keto-Bmt1]-Val2)-cyclosporine, a cyclosporine D derivative, and cyclosporine A (Sandimmune™), were provided by Sandoz Pharmaceutical Corp. (Novartis), East Hanover, N.J. Stock solutions of PSC 833 and cyclosporine A (10 mM) were prepared in ethanol. All stock solutions were prepared in 1-dram glass vials with Teflon-lined screw caps and stored at −20° C. Culture media containing drugs were prepared just prior to use. Vehicles (ethanol, acetone) were present in control (minus drug) cultures at final concentrations of 0.01–0.1%.

6.13.1b. Methods for Examples 8–11

Materials. [H]UDP-Glucose (40 Ci/mmol) was purchased from American Radiolabeled Chemicals (St. Louis, Mo.). EcoLume (liquid scintillation cocktail) was from ICN (Costa Mesa, Calif.), and α-$^{32}$P-dCTP (6,000 Ci/mmol) was from Amersham (Arlington Heights, Ill.). $C_6$-Ceramide (N-hexanoylsphingosine) was purchased from LC Laboratories (Woburn, Mass.). Sulfatides (ceramide galactoside 3-sulfate) were from Matreya (Pleasant Gap, Pa.), and phosphatidylcholine (1,2-dioleoyl-sn-glycero-3-phosphocholine) was from Avanti Polar Lipids (Alabaster, Ala.). C219, monoclonal antibody against human P-glycoprotein, was from Signet Laboratories (Dedham, Mass.), and Bcl-2 (Ab-1) monoclonal antibody against human Bcl-2 was from Oncogene Research Products (Cambridge, Mass.). Hygromycin B was purchased from Boehringer Mannheim (Indianapolis, Ind.). Doxycycline hydrochloride, adriamycin (doxorubicin hydrochloride), and other chemicals were purchased from Sigma (St. Louis, Mo.). FBS was purchased from HyClone (Logan, Utah). RPMI medium 1640 and DMEM medium (high glucose) were from GibcoBRL (Gaithersburg, Md.), and cultureware was from Corning Costar (Cambridge, Mass.).

Cell Lines and Culture Conditions. Human breast adenocarcinoma cells, MCF-7 and MCF7 AdrR cells (MDR clone) were kindly provided by Dr. Kenneth Cowan and Dr. Merrill Goldsmith (National Cancer Institute, Bethesda, Md.). Cells were maintained in RPMI medium 1640 containing 10% (v/v) FBS (fetal bovine serum), 100 units/ml penicillin, 100 µg/ml streptomycin, and 584 mg/liter L-glutamine. Cells were cultured in a humidified, 5% $CO_2$ atmosphere tissue culture incubator, and subcultured weekly using trypsin-EDTA (0.05%–0.53 mM) solution. Transfected cells, MCF-7/GCS, were cultured in RPMI medium 1640 containing 10% FBS and 200 µg/ml hygromycin in addition to the above components.

pTRE-GCS Expression Vector Construction and Transfection. pCG-2, a Bluescript II KS containing GlcT-1 [Ichikawa, 1996; GCS, glucosylceramide synthase (ceramide glucosyltransferase, UDP-glucose:N-acylsphingosine D-glucosyltransferase, EC 2.4.1.80)] in the EcoR I site was kindly provided by Dr. Shinichi Ichikawa and Dr. Yoshio Hirabayashi (The Institute of Chemical and Physical Research, RIKEN, Saitama, Japan). The gene encoding human glucosylceramide synthase was immune-selected by monoclonal antibody M2590 from a human melanoma cell (SK-Mel-28) library (Ichikawa, 1996). The full-length cDNA of human GCS was subcloned into the EcoR I site in the pTRE, Tet-repressible expression plasmid. The Tet-on gene expression system was purchased from Clontech (Palo Alto, Calif.). This system contains three vectors, pTet-on, pTRE and pTK-Hyg. The pTet-on vector (pUHD17-1neo) expresses a doxycycline-controlled rtTA which is a fusion protein of a reverse Tet (tetracycline) repressor (rTetR) and the C-terminal domain of protein 16 of herpes simplex virus, constitutively expressed under control of human CMV (cytomegalovirus) promoter (Goseen, 1995; Faris, 1996). The pTRE vector (pUHD10-3) contains a MCS (multiple cloning site) to accept any cDNA to be expressed followed by an SV40 polyadenylation sequence (Resnitzky, 1994). The promoter region upstream from the MCS contains a minimal human CMV promoter ($P_{minCMv}$) with heptamerized tet-operators. This promoter is silent in the absence of binding of rtTA (reverse tetracycline transactivator) to the tet-operators. However, when the rTetR of the rtTA binds to the tet-operators, the virion protein 16 domain of the rtTA can activate $P_{minCMV}$ activity to a very high level, and switch on expression of the target gene, GCS. Binding of doxycycline to the rTetR domain of the rtTA can almost completely activate rtTA binding to the promoter (Gossen, 1995; Resnitzky, 1994; Goseen, 1992; Yin, 1996).

Sense-orientation of the GCS cDNA was analyzed with Vector NTI 4.0, and doubly checked by restriction enzyme digestion with Hind III, and Xho I plus Not I. The pTK-Hyg vector, which has a hygromycin-resistant gene under control of the mouse β-globin promoter, was used to select the stable transfectants. When MCF-7 cells reached 20% confluence, pTet-on DNA (10 μg/ml, 100-mm dish) was introduced by co-precipitation with calcium phosphate (Mammalian Transfection Kit, Stratagene, La Jolla, Calif.). The transfected cells were selected in RPMI medium 1640 containing 10% FBS and 400 μg/ml G418. Each G418-resistant clone was screened by luciferase assay, after transient transfection with pTRE-Luc vector containing the reporter gene, luciferase. pTK-Hyg (10 μg DNA) and pTRE-GCS (10 μg DNA) were introduced into the selected MCF-7 Tet-on cells by co-precipitation with calcium phosphate. The GCS-transfected cells were primarily selected in RPMI medium containing 10% FBS and 200 μg/ml hygromycin. As a control for transfection, MCF-7 Tet-on cells were co-precipitated with pTK-Hyg and pTRE plasmid without GCS cDNA.

Transient Transfection and Luciferase Assay. This procedure was performed as previously described (Goseen, 1995; Goseen, 1992; Yin, 1996). After MCF-7 cell transfection with pTet-on vector, each G418-resistant clone was grown for 16 hr in 6-well plates (4,000 cells/well) in 10% FBS RPMI medium, then shifted to 10% FBS DMEM medium. After a 6 hr incubation, pTRE-Luc (1.5 μg DNA) was introduced by co-precipitation with calcium phosphate. After culturing in 10% FBS DMEM medium for 18 hr and in 10% FBS RPMI medium for 48 hr, luciferase activity was measured using a commercial Luciferase Assay System according to the instruction manual (Promega, Madison, Wis.). Incubation for 48 hr in 3.0 μg/ml doxycycline was used to induce expression of rtTA protein. Cellular extracts (100 μg protein) from each clone were used. The activity of luciferase was measured by scintillation spectroscopy 2 min after the addition of substrate. MCF-7 cells transfected with pTRE-Luc were used as controls.

Glucosylceramide Synthase Assay. To determine the expression of GCS in the hygromycin-resistant clones, a modified radioenzymatic assay was utilized (Lavie, 1997; Shukla, 1990). After incubation in the absence or presence of doxycycline (3 μg/ml, 48 hr), cells were homogenized by sonication in lysis buffer (50 mM Tris-HCl, pH 7.4, 1.0 μg/ml leupeptin, 10 μg/ml aprotinin, 25 μM PMSF). Microsomes were isolated by centrifugation (129,000×g, 60 min). The enzyme assay, containing 50 μg microsomal protein, in a final volume of 0.2 ml, was performed in a shaking water bath at 37° C. for 60 min. The reaction contained liposomal substrate composed of $C_6$-ceramide (1.0 mM), phosphatidylcholine (3.6 mM, MW 786.15), and brain sulfatides (0.9 mM, MW 563). The liposomal substrate was prepared by mixing the components, evaporating the solvents under a stream of nitrogen, and sonicating in water over ice for 1-min using a microtip at 50% output (Kontes, Micro Ultrasonic Cell Disrupter). Other reaction components included sodium phosphate buffer (0.1 M) pH 7.8, EDTA (2.0 mM), $MgCl_2$ (10 mM), dithiothreitol (1.0 mM), β-NAD (2.0 mM), and [$^3$H]UDP-glucose (0.5 mM). Radiolabeled and unlabeled UDP-glucose were diluted to achieve the desired radiospecific activity (4,700 dpm/nmol). To terminate the reaction, tubes were placed on ice and 0.5 ml isopropanol and 0.4 ml $Na_2SO_4$ were added. After brief vortex mixing, 3 ml t-butyl methyl ether was added and the tubes were mixed for 30 sec. After centrifugation, 0.5 ml upper phase which contained GC, was withdrawn and mixed with 4.5 ml EcoLume for analysis of radioactivity by liquid scintillation spectroscopy.

Analysis of Ceramide and Glucosylceramide. Analyses were performed as previously described (Lavie, 1997). Cellular lipids were radiolabeled by incubating cells with [$^3$H]palmitic acid (2.5 μCi/ml culture medium) for 24 hr. After removal of medium, cells were rinsed twice with PBS (pH 7.4), and lipids were extracted (Lavie, 1997). After nitrogen evaporation of solvents, total lipids were resuspended in 100 μl of chloroform /methanol (1:1, v/v), and aliquots were applied to TLC plates. Ceramide was resolved using solvent system I, which contained chloroform/acetic acid (90:10, v/v). GC was resolved using solvent system II, which contained chloroform/methanol /ammonium hydroxide (70:20:4, v/v). Commercial lipid standards were co-chromatographed. After development, lipids were visualized by iodine vapor staining, and areas of interest were scraped into 0.5 ml water. EcoLume counting fluid (4.5 ml) was added, the samples were mixed, and radioactivity was quantitated by liquid scintillation spectrometry.

RNA Analysis. RNA was extracted from cells using the single-step method described by Chomczynski and Sacchi (Chomczynski, 1987). Equal amounts of total RNA (15 μg) were denatured in 59% formamide/2.2 M formaldehyde, size separated by electrophoresis on 1% agarose-formaldehyde, and then blotted onto nitrocellulose-plus (Sambrook, 1989). GCS cDNA was prepared from pCG-2 plasmid, digested with EcoR I, and Hind III (Stratagene, La Jolla, Calif.). The 1.1 kb fragment was then isolated by 1% low-melt agarose electrophoresis using a commercial agarose gel DNA extraction kit (Boehringer Mannheim). Probing of $^{32}$P-GCS cDNA was performed by nick translation according to the instruction manual (Boehringer Mannheim). Nitrocellulose-plus membranes were hybridized with the 32P-GCS probe at 68° C. for 18 hr. The filters were exposed at −70° C. for autoradiography. For even gel loading, 28 S RNA was stained with ethidium bromide and used as a control.

Cytotoxicity Assay. The assay was performed as previously described (Lavie, 1997). Briefly, after culture in the absence or presence of 3.0 μg/ml doxycycline for 48 hr, cells were harvested and seeded in 96-well plates (2,000 cells/well), in 0.1 ml RPMI-1640 medium containing 10% FBS in the absence or presence of 3.0 μg/ml doxycycline. Cultures were incubated at 37° C. for 24 hr before addition of drug. Drugs were added in FBS-free medium (0.1 ml), and cells were cultured at 37° C. for the indicated periods. Drug cytotoxicity was determined using the Promega 96 Aqueous cell proliferation assay kit. Absorbance at 490 nm was recorded using an ELISA reader (Molecular Devices, San Diego, Calif.).

Western Blot Analysis. Western blots were performed using a modified procedure (Yang, 1996; Blagosklonny, 1996). Confluent cells were washed twice with PBS containing 1.0 mM PMSF, and detached with trypsin-EDTA solution. Cells were pelleted by centrifuging at 500×g for 5 min. Cell pellets were solubilized in 1.0 ml of cold TNT buffer (20 mM Tris-HCl, pH 7.4, 200 mM NaCl, 1% Triton X-100, 1 mM PMSF, 1% aprotinin) for 60 min with shaking. The insoluble debris was excluded by centrifugation at 12,000×g for 45 min at 4° C. The detergent soluble fraction was loaded in equal aliquots by protein and resolved using 4–20% gradient SDS-PAGE. The transferred nitrocellulose blot was blocked with 3% fat-free milk powder in TBST (10 mM Tris-HCl, pH 8.0, 150 mM NaCl, 0.05% Tween-20) at room temperature for 1 hr. The membrane was then immuno-blotted with monoclonal antibodies, C219 (5 $\mu$g/ml) or Bcl-2 (Ab-1) (2.5 $\mu$g/ml) in TBS containing 0.5% BSA (10 mM Tris-HCl, pH 8.0, and 150 mM NaCl) at 4° C. for 18 hr. Detection using enzyme-linked chemiluminescence was performed using ECL (Amersham).

Statistics. All data represent the mean ±SD. Experiments were repeated two or three times. Student's t-test was used to compare mean values, and linear correlation between variables was tested using Pearson's correlation coefficient.

6.13.2. Example 1

Effect of PSC 833 and Cyclosporine A on Glycolipid Metabolism

Figure 2:
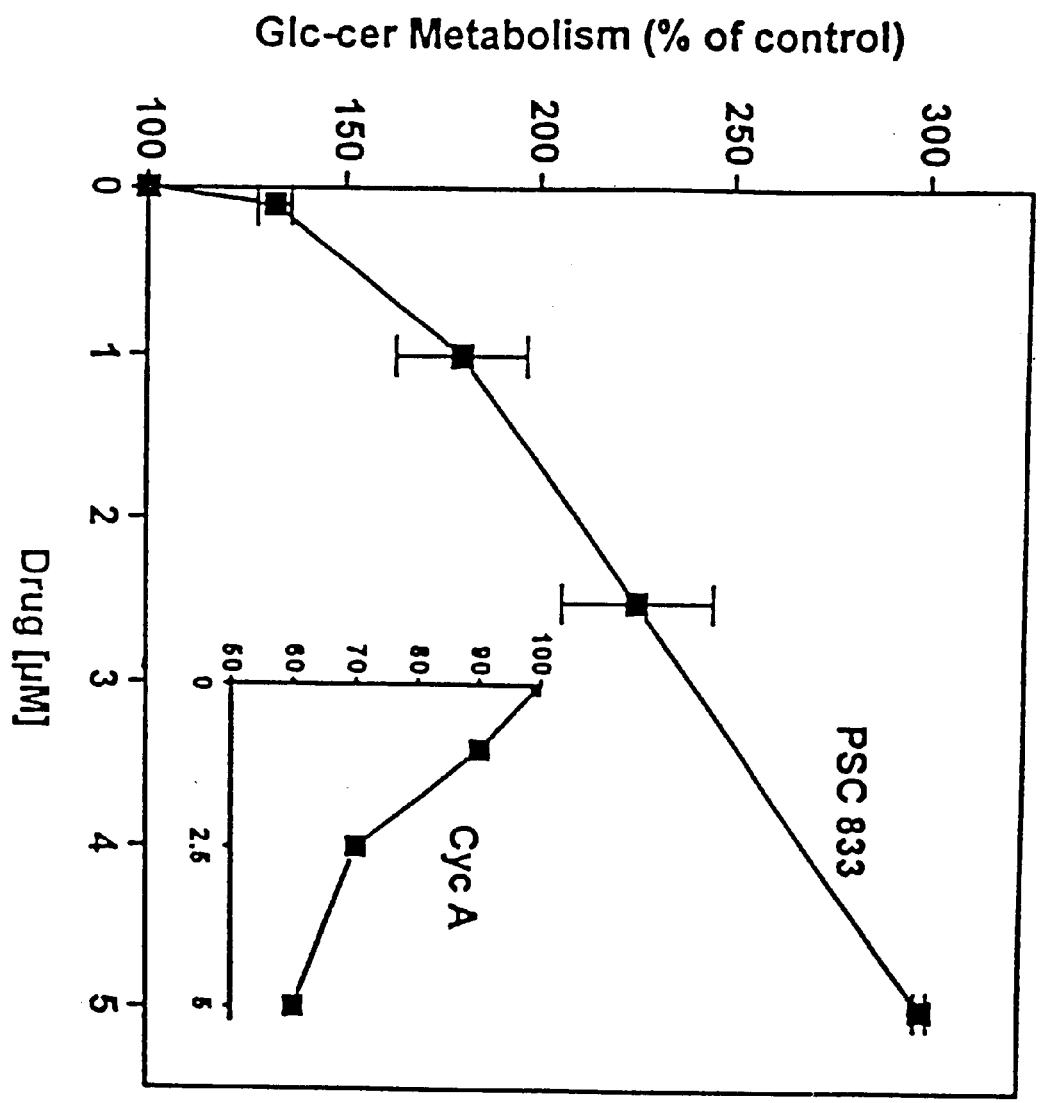
Figure 3:
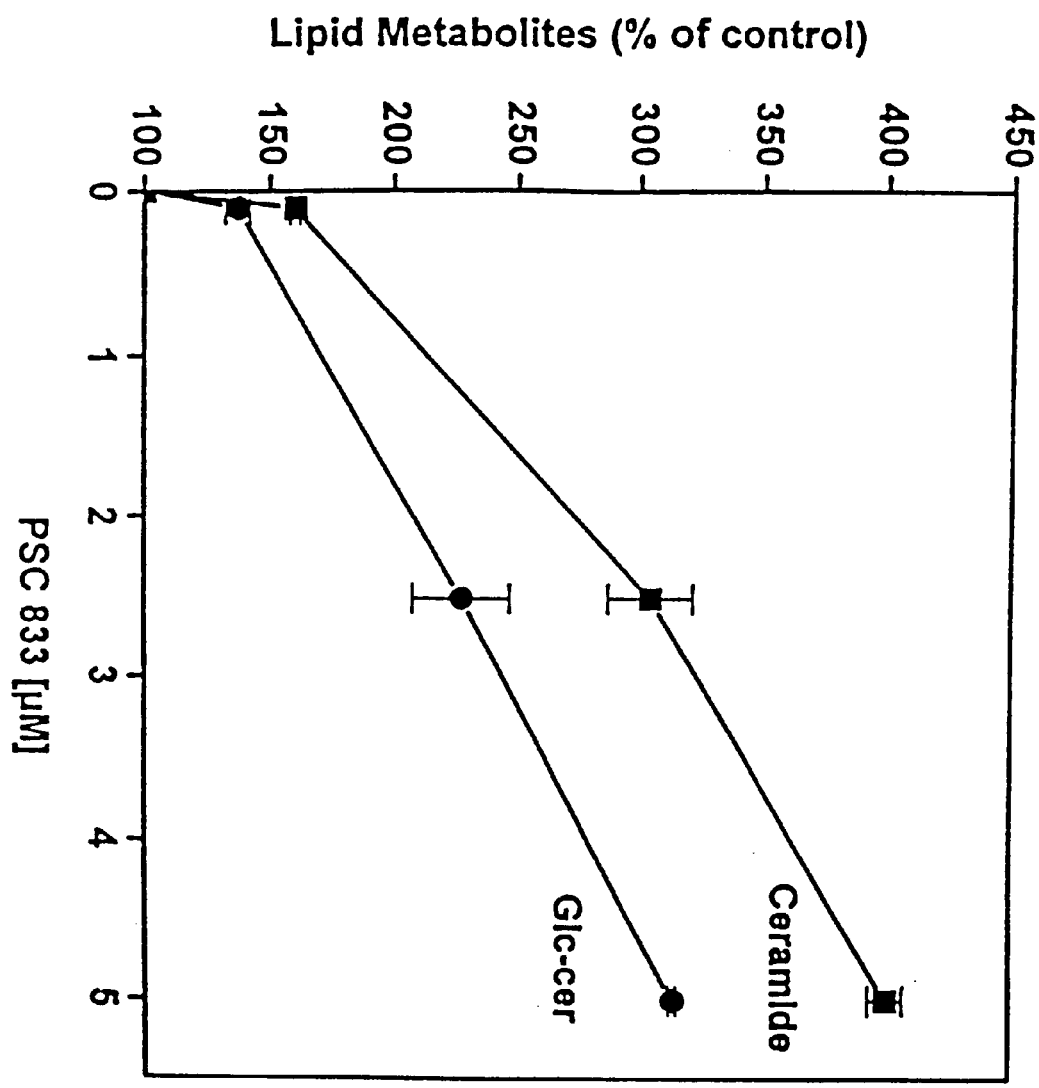

The effects of cyclosporine A and PSC 833 on glucosylceramide levels in MDR breast cancer cells were analyzed. The TLC autoradiograph in FIG. 1 illustrates the influence of the two cyclosporine-derived MDR modulators on glycolipid metabolism. MCF-7-AdrR cells (10 cm dishes) were grown overnight in medium containing [$^3$H]serine (2.0 $\mu$Ci/ml 5% FBS medium) and either cyclosporine A (5.0 $\mu$M) or PSC 833 (2.5 $\mu$M). Lipids were extracted and analyzed by TLC autoradiography as described in the Methods section. The solvent system used was chloroform/methanol/ammonium hydroxide (80:20:2, v/v/v). Glucosylceramide, which migrates as a doublet on TLC (due to chemical diversity of the ceramide moiety), was nearly depleted in cells that were exposed to cyclosporine A; however, upon exposure to PSC 833 glucosylceramide levels increased markedly (FIG. 1). The opposing effects of these agents on glycolipid metabolism is readily seen in the PSC 833 dose-response data of FIG. 2. Cells, seeded into 6-well plates, were grown for 2-days ($\approx$60% confluent) and treated with either cyclosporine A or PSC 833 at the concentrations indicated for 60 min before the addition of [$^3$H]palmitic acid (0.9 $\mu$Ci/ml medium) for an additional 23 h. Total lipids were extracted and glucocerebroside was quantitated by TLC and LSC as described in Methods. Whereas increasing the concentration of cyclosporine A inhibited glucosylceramide formation (FIG. 2, inset), increasing the concentration of PSC 833 resulted in glucosylceramide synthesis (FIG. 2). Activation of glucosylceramide formation was apparent at levels of PSC 833 as low as 0.1 $\mu$M. The dose-response data is illustrated in FIG. 3. MCF-7-AdrR cells were seeded into 6-well plates. At $\approx$60% confluence, cells were treated with PSC 833 at the concentrations shown for 60 min before the addition of [$^3$H] palmitic acid for an additional 23 h. Total cellular lipid extracts were analyzed for [$^3$H]ceramide and [$^3$H] glucosylceramide by TLC and LSC. FIG. 3 illustrates that PSC 833 elicited an increase in cellular ceramide formation that preceded the increase in glucosylceramide formation.

Figure 4:
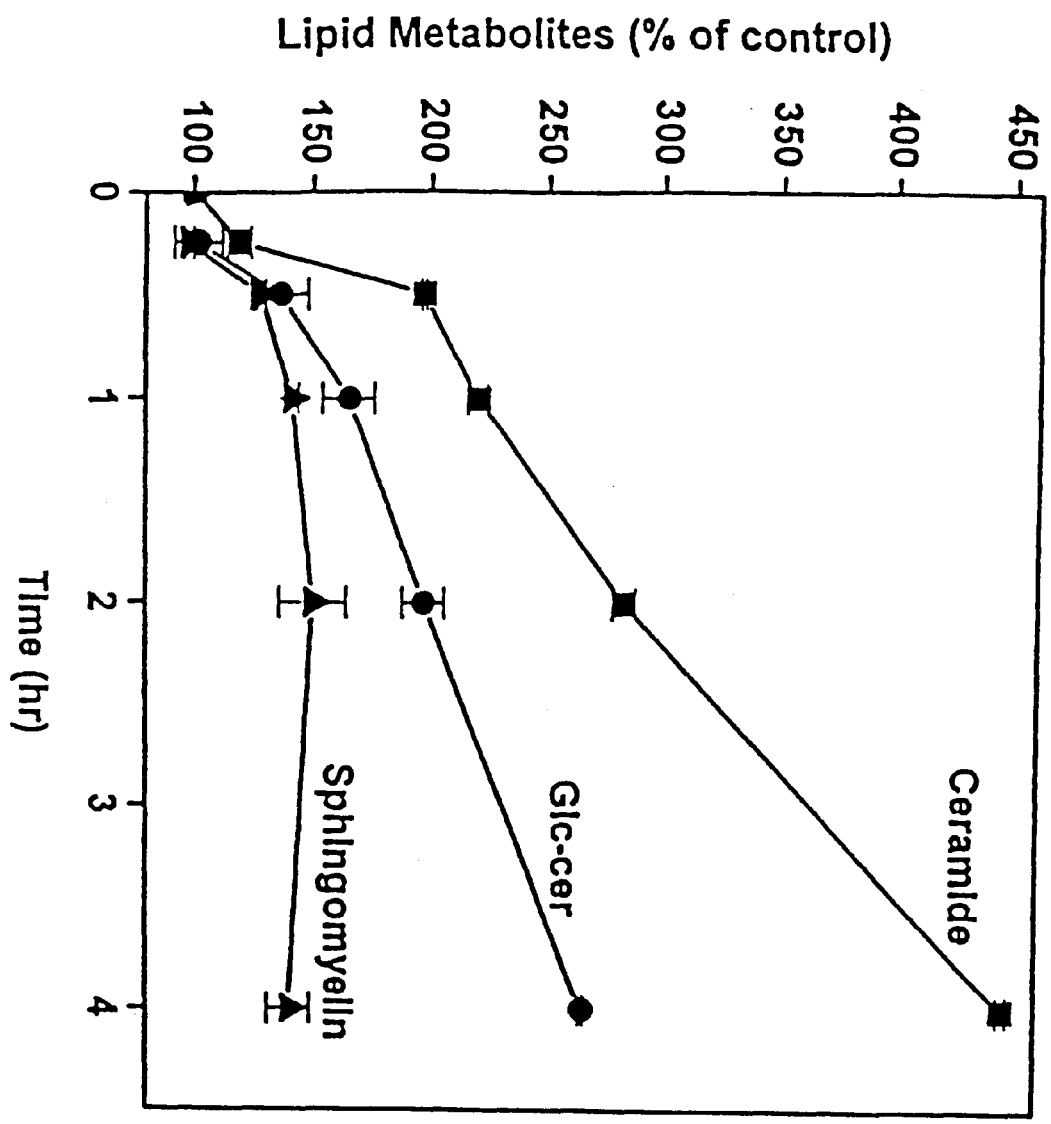

We also tested the influence of exposure time (15 min–4 h) on the metabolism of ceramide, glucosylceramide, and sphingomyelin. MCF-7-AdrR cells were seeded into 6-well plates and at $\approx$70% confluence [$^3$H]palmitic acid (1.0 $\mu$Ci/ml medium) and PSC 833 (5.0 $\mu$M) were added simultaneously for the times indicated. Lipids were extracted and ceramide, glucosylceramide (Glc-cer), and sphingomyelin were analyzed by TLC and LSC as described in the Methods section. FIG. 4 illustrates that activation of cellular ceramide formation was discernible as early as 30 min after cells were given PSC 833, and at all times thereafter the rates of ceramide synthesis preceded the rates of glucosylceramide formation. Sphingomyelin, which contains ceramide, also increased in response to PSC 833; however, the increases were a modest 150% of control at 2 h.

6.13.3. Example 2

Effect of PSC 833 on Adriamycin Efficacy in MDR Breast Cancer Cells

Figure 5:
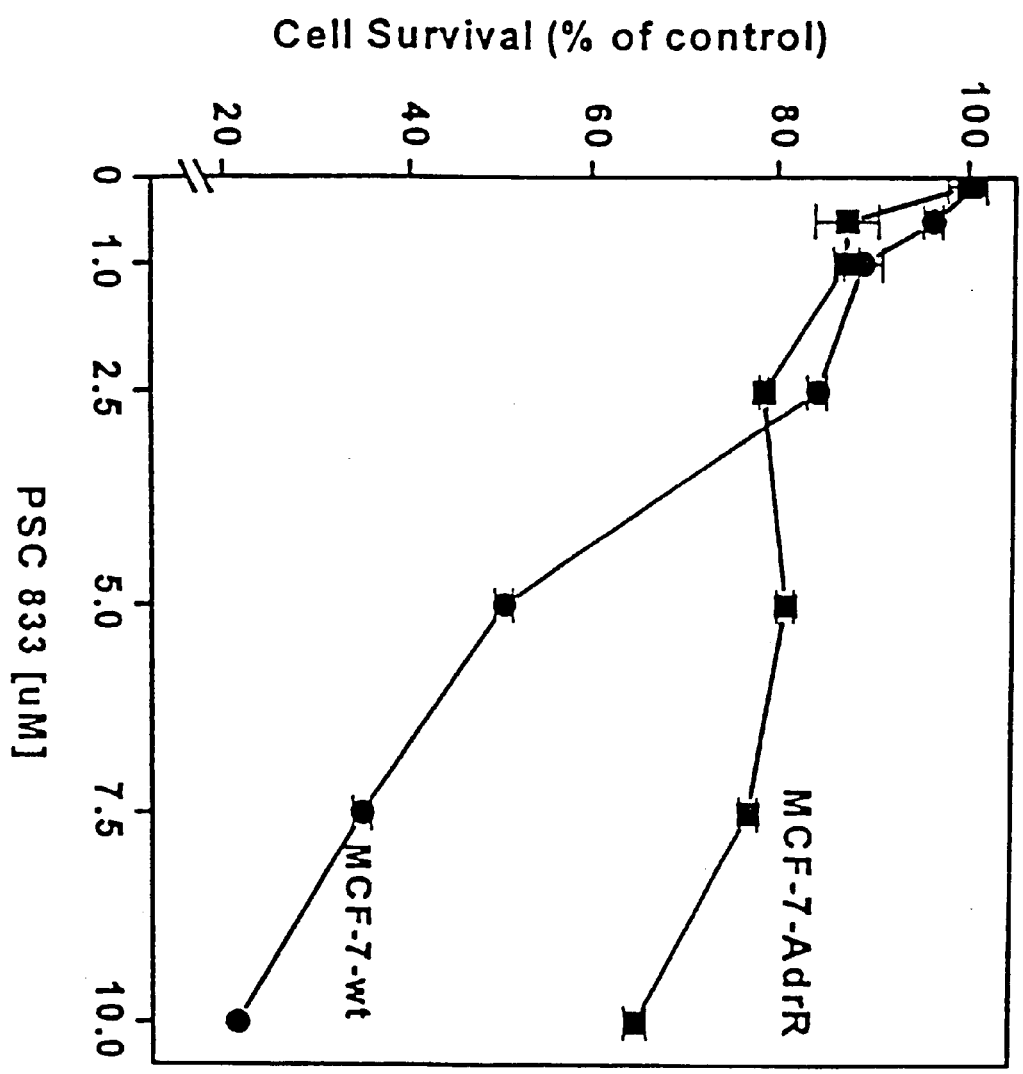
Figure 6:
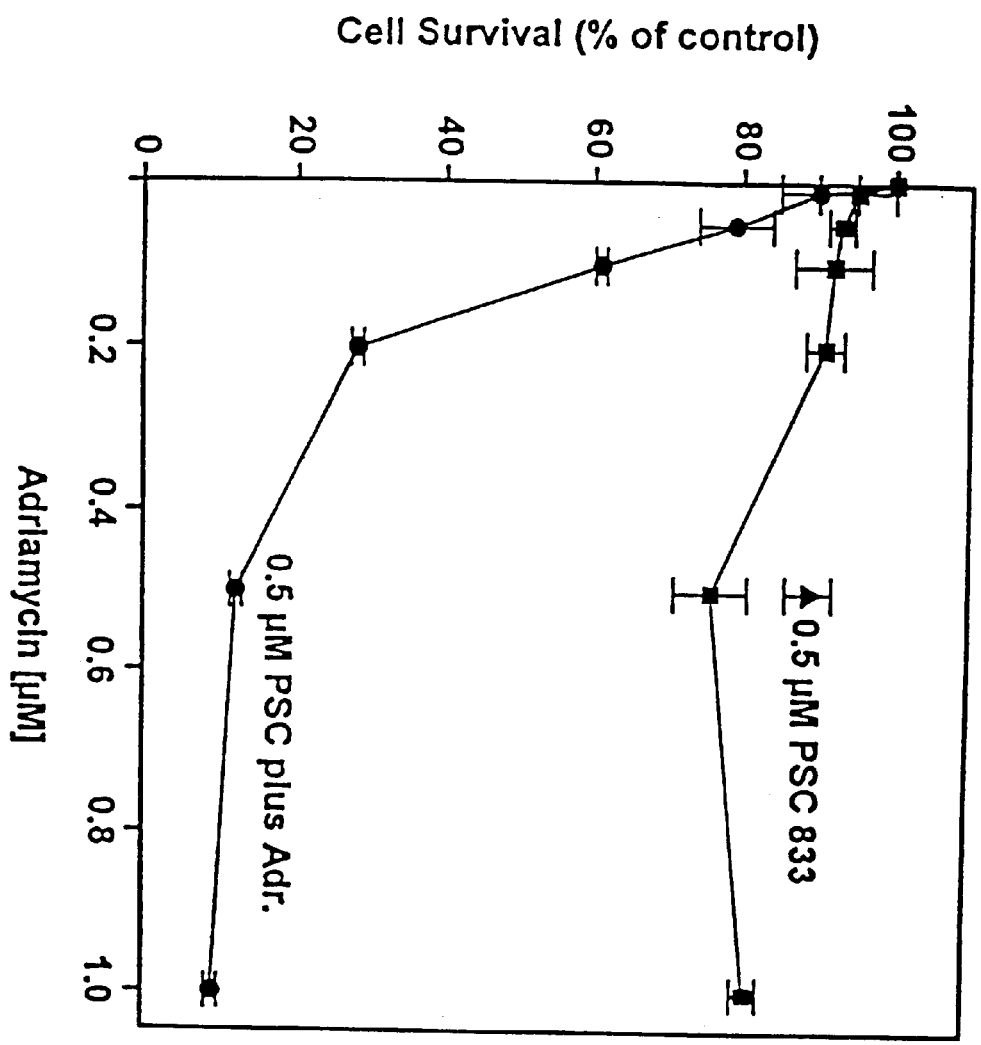

Comparing drug sensitive (wild-type, wt) with MDR cells, the data of FIG. 5 show that MDR cells are more resistant to PSC 833 toxicity. MCF-7-wt (wt, chemosensitive) and MCF-7AdrR cells were seeded into 96-well plates, 2,000 cells/well, and treated the following day with PSC 833 at concentrations of 0.1–10 $\mu$M. Four days later cell survival was measured using the Promega cell proliferation assay as described in the Methods section. Each point represents the average of six replicate assays. At higher concentrations (10 $\mu$M), MDR cell survival was only lowered by 35%, whereas wt cells were more sensitive (80% reduction in cell survival). Assessing the MDR modulatory action of PSC 833, when given at low dose (0.5 $\mu$M) in combination with adriamycin, MDR cell survival was greatly reduced (FIG. 6). MCF-7-AdrR cells were seeded into 96-well plates (2,500 cells/well) and treated 24 h later with vehicle, adriamycin at the increasing concentrations (●). Cell viability was determined using the Promega assay, after 5-days incubation in the presence of drugs (FIG. 6). Each experimental point represents the average of six replicate assays. The data in FIG. 6 demonstrate that MCF-7-AdrR cells are essentially refractory to adriamycin. Over a concentration range of 0.1–1.0 $\mu$M adriamycin, cell survival was within 80–95% of control values (FIG. 6). PSC 833, at a concentration of 0.5 $\mu$M, elicited only a 10% kill. However, when PSC 833 was kept constant (0.5 $\mu$M) and escalating doses of adriamycin were given, cell viability dropped precipitously (FIG. 6). At 0.2 $\mu$M adriamycin (FIG. 6, upper curve), cell survival (90%) was on a parallel with survival of cells exposed to 0.5 $\mu$M PSC 833 alone. When the two agents were mixed, cell survival fell to 28% (FIG. 6, lower curve).

6.13.4. Example 3

Combination Therapy of PSC 833 with Adriamycin and Tamoxifen

Figure 7:
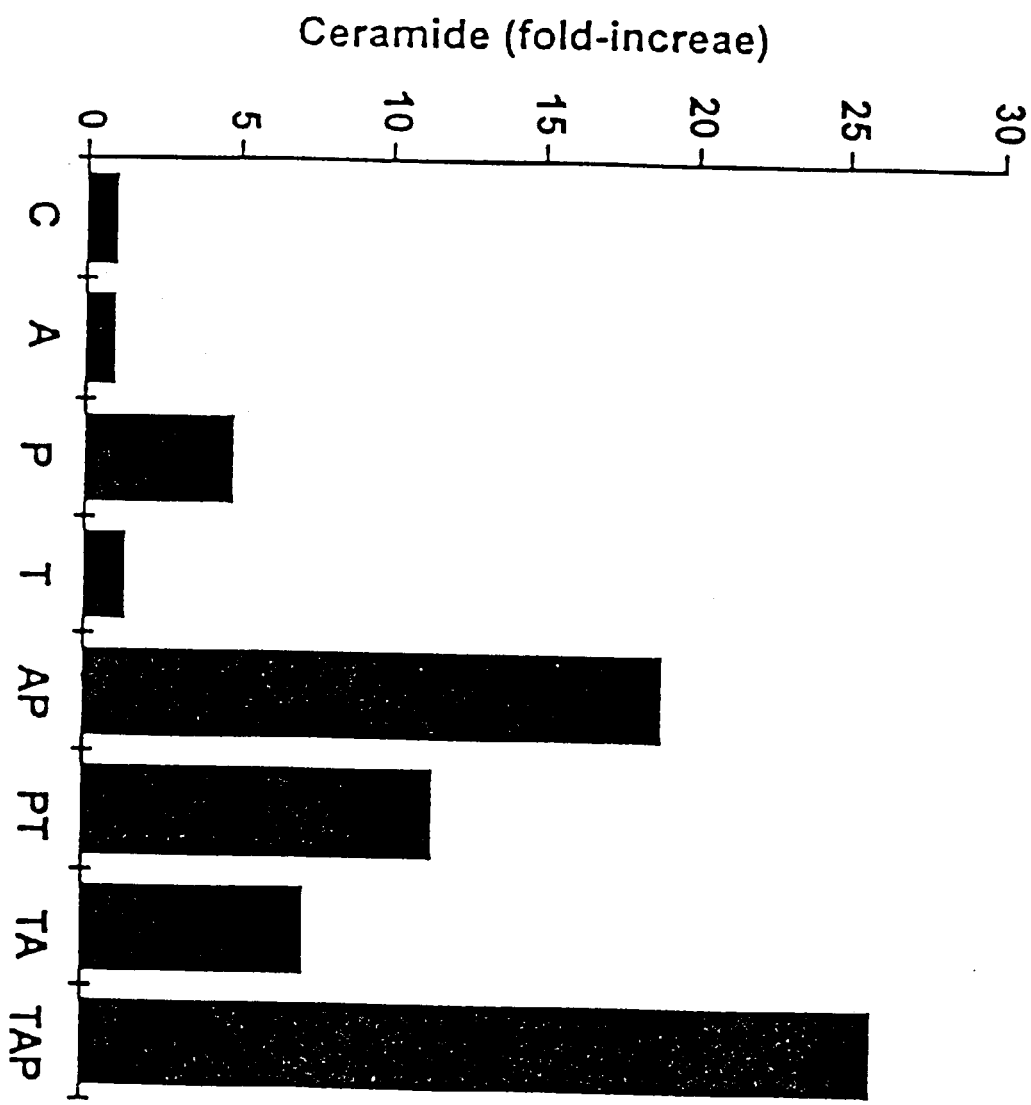
Figure 8:
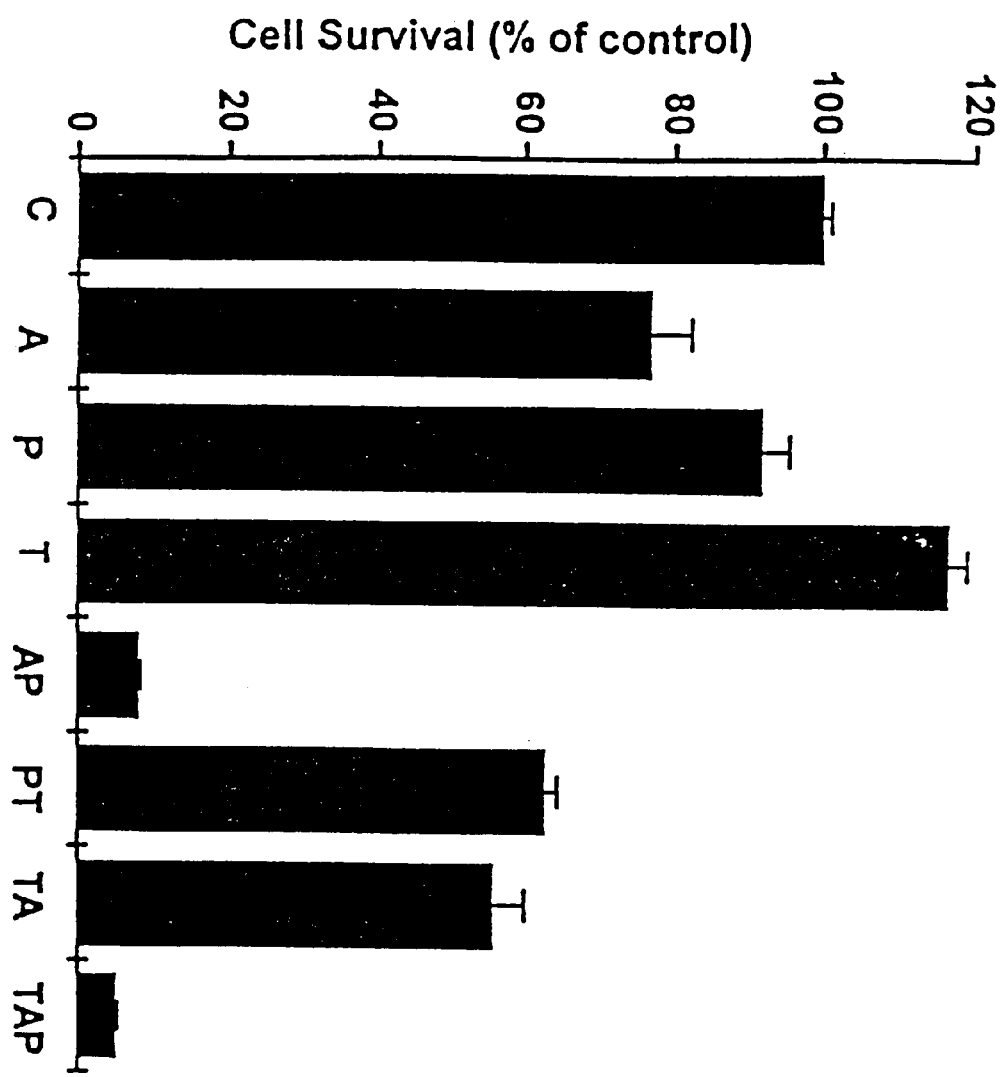

The data of FIG. 7 reveal that combination therapeutics have a marked impact on ceramide production. MCF-7-AdrR cells were seeded into 6-well plates and at 60–70% confluence, cells were treated with vehicle (control), adriamycin (2.5 EM), PSC 833 (5.0 $\mu$M), tamoxifen (5.0 $\mu$M) or combinations indicated for 24 h in the presence of [$^3$H] palmitic acid (1.0 $\mu$Ci/ml culture medium). Lipids were extracted and ceramide was analyzed by TLC in a solvent system containing chloroform/acetic acid (90:10, v/v) followed by LSC for tritium quantitation. Data points represent the average of triplicate experiments. FIG. 7 illustrates that cells exposed to adriamycin alone, ceramide formation was not influenced. PSC 833 caused a 4.8-fold increase in ceramide levels, and tamoxifen, by itself, caused a moderate 0.3-fold increase in ceramide. When adriamycin and PSC 833 were co-administered, ceramide levels rose to 19-times control values, and likewise, with mixtures of PSC 833 plus tamoxifen and tamoxifen plus adriamycin, ceramide levels increased to 11.5-fold and 7.3-fold over control values, respectively. A combination of the three drugs (TAP) produced the highest elevation in ceramide, 26-fold over control. In evaluating cell viability among the various drug regimens studied, it was shown that drug combinations eliciting the greatest elevation in ceramide were highly cytotoxic (FIG. 8). MCF-7-AdrR cells were seeded into 96-well plates at 2,000 cells/well and treated the following day with the indicated drugs: control (vehicle); A, adriamycin (2.5 $\mu$M); P, PSC 833 (5.0 EM); T, tamoxifen (5.0 $\mu$M), or the combinations shown. After 3-days of exposure, cell viability was evaluated using the Promega assay described in the Methods section. The results show that adriamycin was slightly growth-inhibitory (23%), PSC 833 was without influence, and tamoxifen produced moderate growth stimulation (FIG. 8). Combinations of PSC 833 plus tamoxifen and tamoxifen plus adriamycin reduced cell viability to approximately 50%. The adriamycin-containing mixtures, adriamycin plus PSC 833, and TAP brought cell viability to zero.

Figure 9:
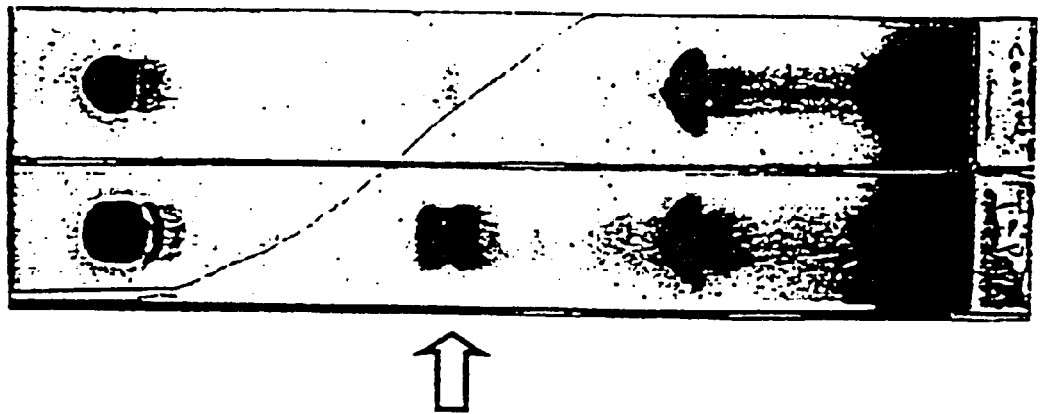
FIG. 9 illustrates the influence of PSC 833 combination chemotherapy on ceramide mass in MCF7-AdrR cells. Combination therapy (right lane) consists of Tamoxifen and Adriamycin and PSC833.

Steady-state radiolabeling of cells with long chain fatty acids is usually achieved by 24 hours. Therefore, the percent incorporation of tritium into complex cellular lipids can be reflective of actual mass changes in the lipids being evaluated. In the experiment shown in FIG. 7, the TAP drug regimen elicited a 26-fold increase in ceramide labeling over control cells. Using the total lipid cpm it was calculated that ceramide radioactivity accounted for 0.5% of total lipid tritium in control cultures and 14% of total lipid tritium in TAP-treated cultures. The magnitude of impact affected by TAP on cellular ceramide levels was confirmed by comparing ceramide on a mass basis. Cells, seeded into 10 cm dishes, were grown to 70–80% confluency. Fresh medium containing 5% FBS and the indicated drugs were then added for 24 h. The TAP-treated cultures contained T, tamoxifen (5.0 $\mu$M); A, adriamycin (2.5, $\mu$M); P, PSC 833 (5.0, $\mu$M). Total cells lipids were extracted, and after gravimetric analysis 200 $\mu$g total lipid from each experimental group was spotted onto TLC plates. The chromatogram was developed in chloroform/acetic acid (90:10, v/v), airdried, sprayed with 30% $H_2SO_4$, and charred in an oven at 180° C. for 20 min. FIG. 9 illustrates the chromatogram, showing the control sample in the left lane and the sample treated with TAP in the right lane, illustrating that ceramide was nearly undetectable in untreated controls, as would be expected for this intermediately complex glycosphingolipids. However, in cells treated with TAP, ceramide mass increased strikingly.

6.13.5. Example 4

Effect of PSC 833 on Ceramide Metabolism in Vinblastine Resistant Epidermoid Carcinoma Cells To determine whether the influence of PSC 833 on ceramide metabolism was restricted to certain cell types, a vinblastine resistant epidermoid carcinoma, KB-V-1, was tested. In KB-V-1 cells exposed to 5.0 $\mu$M PSC 833 for 24 h, cellular levels of tritiated ceramide ([$^3$H]palmitic acid labeling) increased 8.7-fold over untreated cells. This is 4-fold higher than the ceramide increase elicited by PSC 833 in MCF-7-AdrR cells (FIG. 7). The increase in ceramide in KB-V-1 cells was accompanied by cytotoxicity, which while not measured was estimated at 80% cell death. Additionally, the PSC 833-induced increase in [$^3$H]ceramide was not accompanied by decreases in [$^3$H]sphingomyelin, but rather a slight increase in radiolabeled sphingomyelin (33% over the control). These data demonstrate that whereas different cell lines display dissimilar sensitivity to PSC 833 (FIG. 5 and KB-V-1 data), there is none-the-less a common effect on ceramide metabolism.

6.13.6. Example 5

Figure 10:
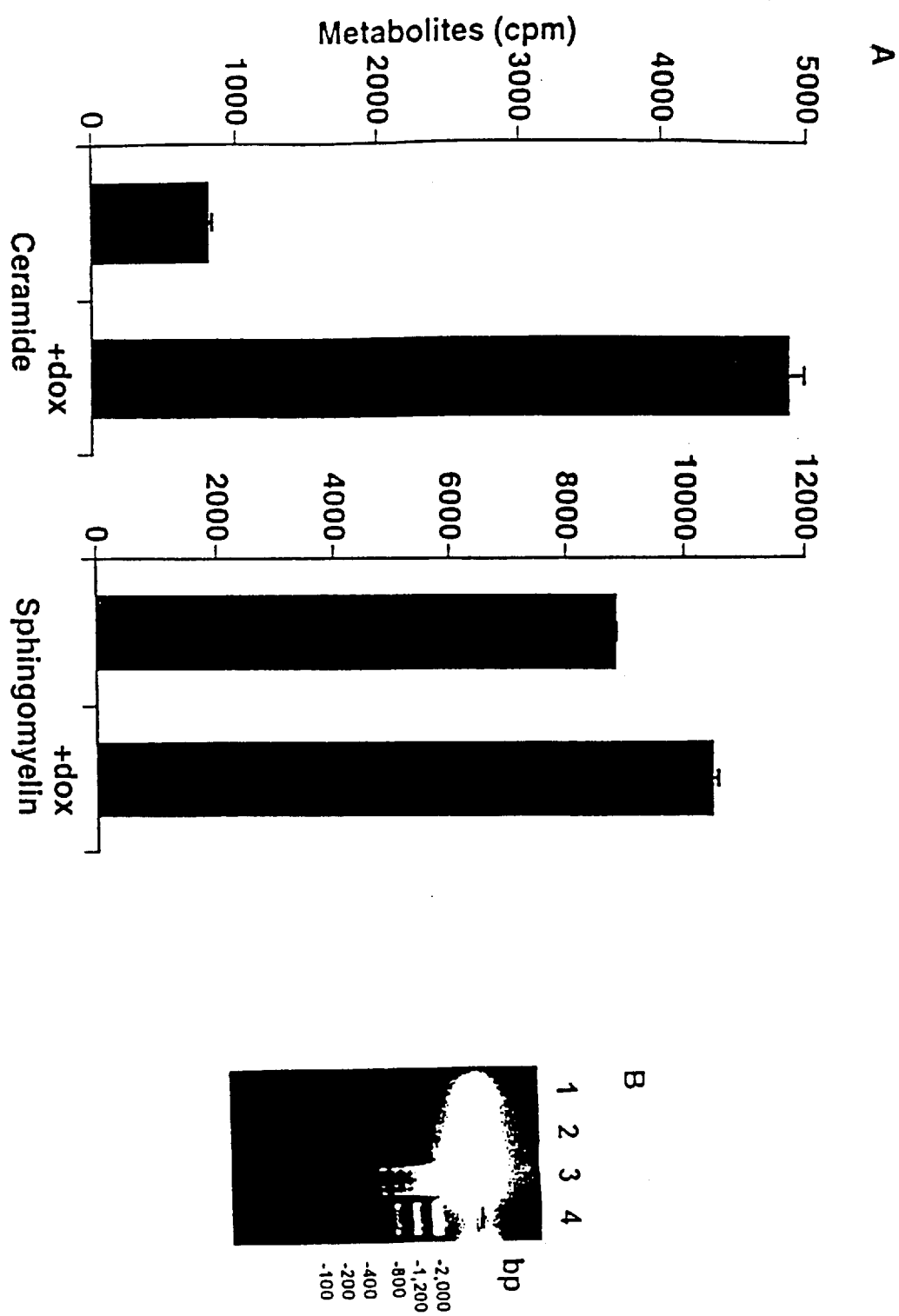
FIGS. 10A–10B illustrates the influence of doxorubicin on lipid metabolism and apoptosis in MCF-7 wild-type cells. (A) Induction of ceramide formation. (B) Induction of apoptosis, as shown by oligonucleosomal DNA fragmentation.

Influence of Doxorubicin on Lipid Metabolism and Apoptosis in MCF-7 Wild-Type Cells The effect of anthracyclines such as doxorubicin on ceramide formation is illustrated in FIG. 10A. Cells were seeded in 6-well plates (80,000 cells/well) in 2.0 ml medium containing 5% FBS. After 2 days of growth, cells were given doxorubicin (1.7 $\mu$M) and [$^3$H]palmitic acid (2.0 $\mu$Ci/well) for 72 hr. Total cell lipids were extracted (Bligh and Dyer, 1959) and analyzed by applying 150,000 cpm (for ceramide analysis) and 50,000 cpm (for sphingomyelin analysis) from each sample to the origin of a Silica Gel G TLC plate and resolving [$^3$H]ceramide and [$^3$H]sphingomyelin as described in the Methods section. The "+ dox" notation indicates that doxorubicin was present. FIG. 10A illustrates that exposure of wild-type human breast cancer cells to doxorubicin (1.7 $\mu$M) caused, after 72 hours, a 6-fold increase in ceramide. In contrast, sphingomyelin production increased only slightly in white cells upon exposure to doxorubicin (FIG. 10A). As expected the increase in ceramide formation gave rise to apoptosis, as shown by trademark DNA laddering illustrated in FIG. 10B. Control and doxorubicin treated (1.7 $\mu$M) cells were grown in 10 cm culture dishes for 72 hr. Cells were harvested by trypsin-EDTA, centrifuged then incubated with digestion buffer (100 mM NaCl, 25 mM EDTA, 10 mM Tris-HCl, 0.5% SDS, 0.3 mg/ml Proteinase K, pH 8.0) at 45° C. for 18 hrs. DNA was extracted with phenol/chloroform/isoamyl alcohol (25:24:1, v/v/v) and precipitated in 1/3 volume 7.5 M ammonium acetate and 2 volume2 100% ethanol at −20° C. overnight. The preparation was centrifuged for 20 min at 10,000×g, 4° C. RNA contaminate was digested in buffer containing 10 mM Tris-HCl, 0.1 mM EDTA, 0.1% SDS, and 100 units/ml RNase, at 37° C. for 2 hr. Re-extracted DNA (15 $\mu$g) was analyzed by electrophoresis on a 2% agarose gel in TAE buffer (40 mM Tris-acetate, 1.0 mM EDTA, pH 8.3). DNA fragments were visualized with ethidium bromide under UV light. Lane 1 represents the control sample, lane 2 the doxorubicin treated sample, and lane 3 represents the low mw DNA mass ladder (Gibco BRL).

This limited effect on sphingomyelin metabolism favors a pathway involving doxorubicin-induced de novo synthesis of ceramide, rather than genesis of ceramide via sphingomyelin hydrolysis by sphingomyelinase.

6.13.7. Example 6

Figure 11:
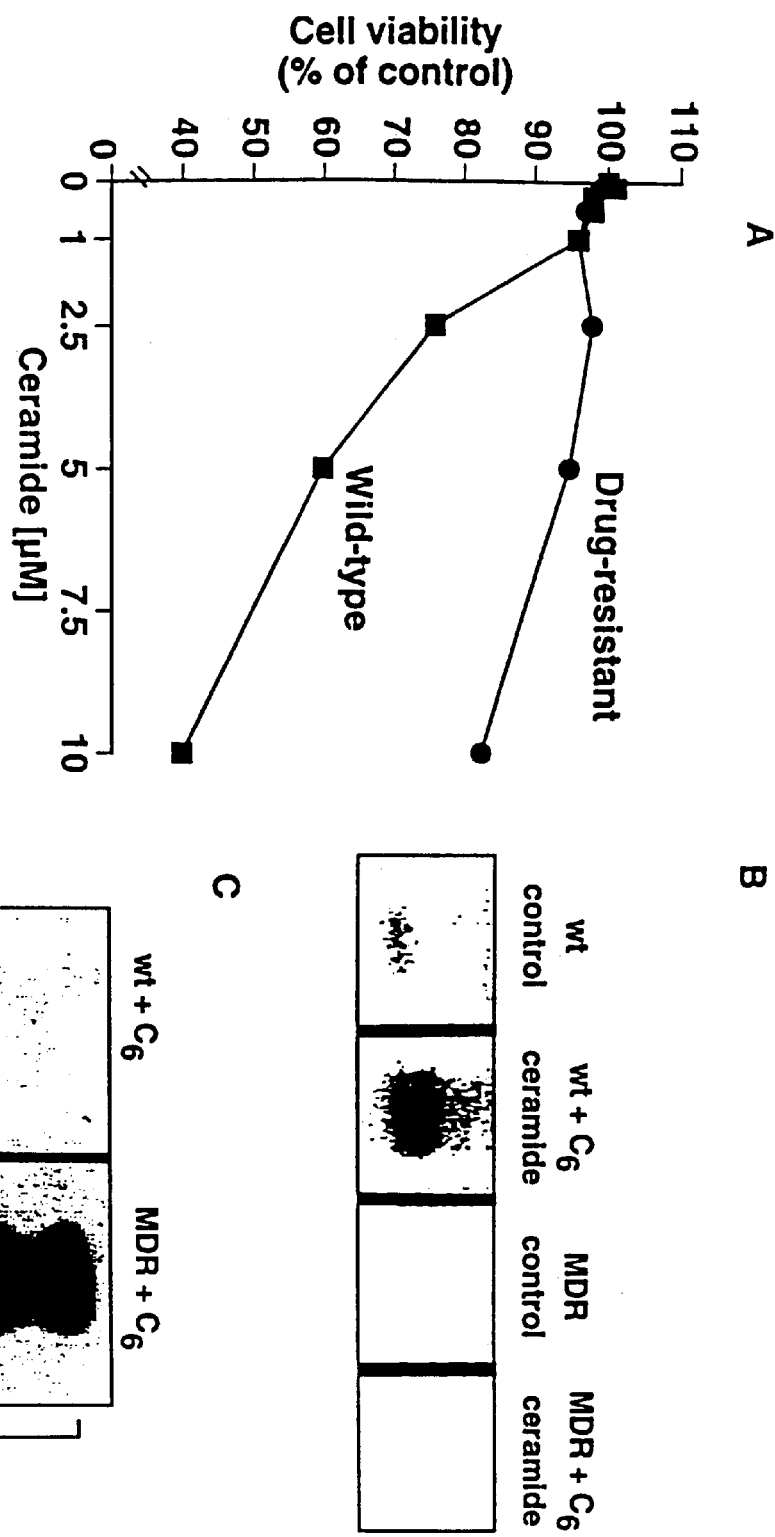
FIGS. 11A–11C shows the cytotoxicity and metabolic fate of ceramide in wild-type and in MDR cells. (A) MDR cells resist ceramide toxicity. (B,C) Metabolic fate of $C_6$-ceramide. arrow in (C) indicates glucosyl-$C_6$-ceramide spot.

Cytotoxicity and Metabolic Fate of Ceramide and its Analog $C_6$Ceramide in Wild-Type and MDR Cells The differential tolerance of wild-type and MDR cancer cells to ceramide and $C_6$ceramide, a cell-permeable analog of ceramide, was evaluated using MCF-7-AdrR cells (human Adriamycin [doxorubicin] resistant breast cancer) and a drug-sensitive counterpart, MCF-7 wild-type. FIG. 11A illustrates the effect of ceramide on MDR cells. Cells (2,000/well) were seeded in 96-well plates in 0.1 ml medium containing 5% FBS and after 24 hr treated with $C_6$ceramide at the concentrations indicated, for 72 hr. Treatment medium was prepared by injecting an ethanolic solution of $C_6$-ceramide into warm medium containing 5% FBS. Cells were given 0.1 ml of the respective $C_6$-ceramide medium; controls received ethanol medium. The ethanol concentration in all wells was 0.15%. Cell viability was determined spectrophotometrically as described in the Methods section. As shown in FIG. 11A, MDR cell growth was relatively uneffected and retained 84% viability in the presence of 10 $\mu$M ceramide, whereas wild-type cells displayed a dose dependent decrease in viability. Subsequent chemical analysis was conducted to determine the intracellular fate of ceramide. The metabolic fate of $C_6$-ceramide is illustrated in FIGS. 11B and 11C. In FIG. 11B, wild-type and MDR cells were seeded in 10 cm tissue culture dishes in medium containing 10% FBS, grown for 3 days, then switched to serum-free medium containing 0.1% BSA minus or plus $C_6$-ceramide (10 $\mu$M) for 24 hr. Total cellular lipids were extracted, and after gravimetric analysis, a 250 $\mu$g aliquot of lipid from each sample was applied to the origin of a TLC plate. $C_6$-Ceramide was resolved in a solvent system containing hexane/diethyl ether/formic acid (30:70:1, v/v/v). Lipids were visualized by $H_2SO_4$ charring. Only the area of the chromatogram corresponding to $C_6$-ceramide ($R_f$ 0.18) is shown. In FIG. 11C, cells were seeded in 10 cm tissue culture dishes as above, and switched to serum-free medium containing 0.1% BSA minus or plus $C_6$-ceramide (10 $\mu$M) for 24 hr. Total cellular lipids were subjected to mild alkaline hydrolysis and 200 $\mu$g (by weight) of the lipid hydrosylate was analyzed by TLC for glucosylceramide and glucosyl $C_6$-ceramide in a solvent system of chloroform/methanol/ammonium hydroxide (70:20:4, v/v/v). Lipid was visualized by $H_2SO_4$ charring. Glucosyl-$C_6$-ceramide ($R_f$ 0.33) is indicated by the arrow.

It was observed that wild-type cells supplemented with $C_6$-ceramide contained abundant free $C_6$-ceramide (FIG. 11B); however, in the MDR cancer cells, free ceramide did not accumulate and was undetectable by comparison (FIG. 11B). The glycosylation product of $C_6$ceramide, glucosyl-$C_6$-ceramide, was markedly increased in MDR cells (FIG. 11C, arrow) compared with wild-type cells which were devoid of both the glycosylated $C_6$-ceramide and the endogenous glucosylceramide doublet (brackets), characteristic of MDR cancers (Lavie, 1996; Lucci, submitted). The chromatographic band corresponding to glucosyl-$C_6$-ceramide, indicates clearly that MDR cells have a markedly enhanced capacity to process ceramide via a glycosylation pathway in contrast with wild-type cancer cells. Uptake of ceramide by MDR cells, as well as the enhanced glycosylation, was confirmed by incubating cells with fluorescently labeled NBD-$C_6$-ceramide (NBD: 7-nitrobenz-2-oxa-1,3-diazole). After 24 hr, the NBD-$C_6$-ceramide, present as NBD-glucosyl-$C_6$-ceramide, was identified in MCF-7 MDR cells but not in wild-type cells.

6.13.8. Example 7

Effect of Combination Therapy with Tamoxifen and Ceramide on MDR Cells

Figure 12:
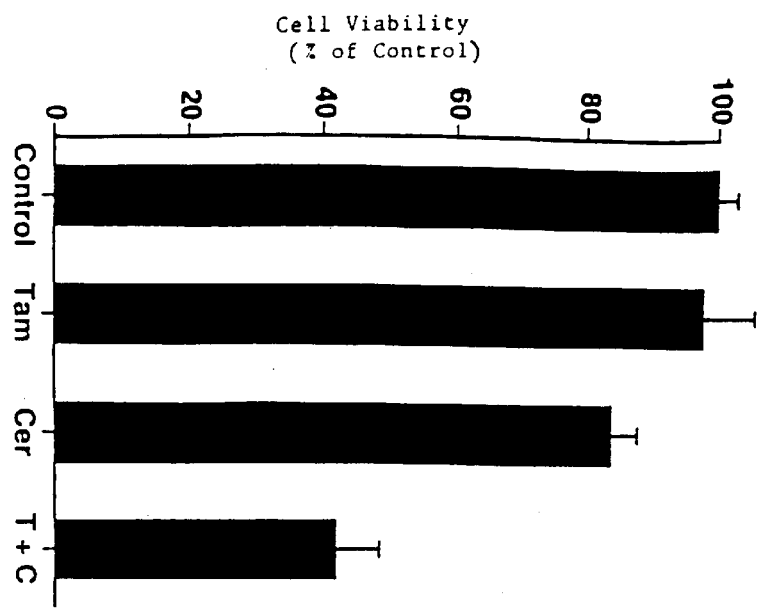
Figure 12:
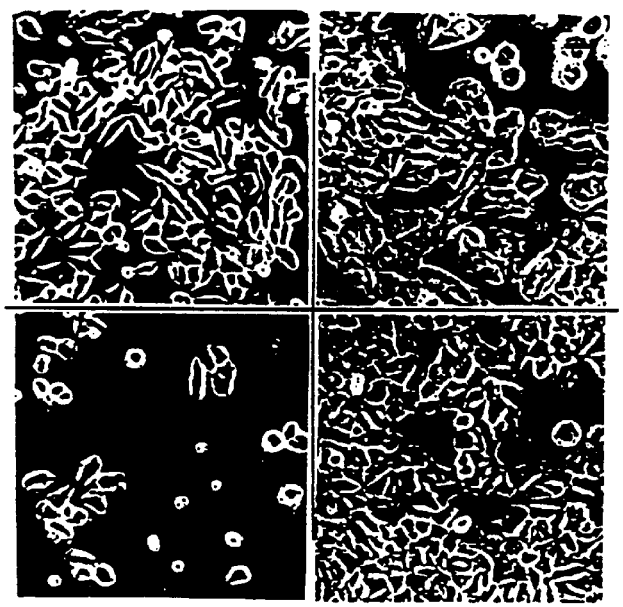
Figure 12:
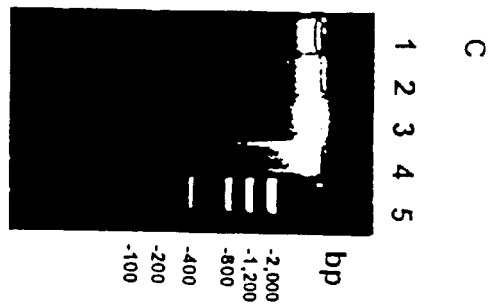

FIG. 12 illustrates direct evidence of the role of tamoxifen as a sensitizer to ceramide toxicity. MCF-7 MDR cells (2,000/well) were seeded in 96-well plates and the following day treated with ethanol vehicle (control), tamoxifen (5.0 $\mu$M), $C_6$-ceramide (5.0 $\mu$M), or a tamoxifen plus ceramide mixture. After 5 days, viability was determined spectrophotometrically as described in the Methods section (FIG. 12A).

FIG. 12B illustrates photomicrographs of MCF-7 MDR cells after various pharmacologic treatments. Cells, 24 hr after subculture in 6 cm dishes, were treated with ethanol vehicle (inset 1), 5.0 $\mu$M tamoxifen (inset 2), 10 $\mu$M $C_6$-ceramide (inset 3), or 5.0 $\mu$M tamoxifen and 10 $\mu$M $C_6$-ceramide (inset 4), for 48 hr.

MDR cells were largely resistant to toxicity when exposed to ceramide (FIG. 11A), and as shown in FIG. 12A, neither tamoxifen nor ceramide alone caused an appreciable reduction in MDR cell viability. Ninety-six percent of cells treated with tamoxifen were viable 72-hr post-treatment, as were 86% of cells treated with $C_6$-ceramide. However, the addition of tamoxifen to the $C_6$-ceramide regimen was clearly cytotoxic (42% viability, FIG. 12A). Therefore, tamoxifen potentiates the cytotoxicity of ceramide in the MDR model. Cells treated with either agent displayed only slight morphologic changes, whereas cells treated with both agents showed gross morphologic changes, reduced proliferation (FIG. 12B), and classical oligonucleosomal DNA fragmentation (FIG. 12C) associated with apoptosis.

6.13.9. Example 8

Expression of Glucosylceramide Synthase

MCF-7 cells were transfected with pTet vector and co-transfected with pTRE-GCS and pTK-Hyg. The stable, high expression clones were selected by screening GCS activity using the cell-free enzyme assay and by Northern blot. After transfection of pTet-on in MCF-7 cells, more than thirty G418-resistant clones were collected. Luciferase activity, which is a measure of expression of rtTA in the G418-resistant clones, was analyzed after three days of transient transfection with pTRE-luciferase vector. After stimulation with doxycycline, maximal expression of luciferase, 16,000-fold above that of MCF-7 cells, was found in clone 16. Luciferase activity in clone 16 in the absence of doxycycline was 15,000-fold higher than that of MCF-7 cells. Clone 1 demonstrated low basal rtTA expression; however, clone 1 was highly responsive to doxycycline, with induced luciferase activity that was 100-fold over MCF-7 cells. Clones 1 and 16 were selected as the optimal MCF-7 Tet-on clones for expression of rtTA.

After co-transfection of pTRE-GCS and pTK-Hyg into clone 1 and clone 16 of MCF-7 Tet-on cells, 65 hygromycin-resistant clones were selected. Utilizing the [$^3$H]UDP-glucose enzyme assay, we analyzed GCS activity, and identified three clones which exhibited 5- to 11-fold increases in enzyme activity (FIG. 13A). Compared with a basal level of 17.2±0.1 pmol GC in MCF-7 wt cells, doxycycline-induced GCS activity in MCF-7/$GCS_{12}$, MCF-7/$GCS_3$ and MCF-7/$GCS_{14}$ was to 167.4±17.2, 183.3±12.4, and 90.2±2.76 pmol GC, respectively (FIG. 13A). There were no differences in either basal or doxycycline-induced GCS activity in transfection control cells (TC) or in the basal level of GCS in MCF-7 wt cells (FIG. 13A). In MCF-7/$GCS_{13}$ and MCF-7/$GCS_{14}$, the doxycycline-inducible GCS activities were 1.6-fold and 4.1-fold, respectively, above untreated cells. The MCF-7/$GCS_{14}$ clone was designated MCF-7/GCS, and this clone was used in further experiments.

Doxycycline-induced GCS mRNA was highly increased in MCF-7/GCS cells compared to doxycycline-naive MCF-7/GCS cells. A representative Northern blot is shown in FIG. 13B. Only traces of GCS mRNA were observed in MCF-7 cells, TC, and MCF-7/GCS cells without doxycycline (FIG. 13B). The levels of ceramide and GC in MCF-7 and in MCF-7/GCS cells were assessed by steady-state radiolabeling of cultured cells using [$^3$H]palmitic acid. As shown in FIG. 13C, transfection with GCS elicited only a moderate decrease in ceramide, compared to MCF-7 cells The decrease was not statistically significant. GC in MCF-7/GCS compared to MCF-7 cells increased slightly, and accounted for 1.8 and 1.5%, respectively, of total cellular radiolabeled lipid.

6.13.10. Example 9

Adriamycin and Ceramide Resistance in Transfected MCF-7/GCS Cells

Some studies have suggested that anthracyclines are may relate to the generation of ceramide, and increased GC may be associated with adriamycin resistance in MDR cells (Bose, 1995; Zyad, 1994; Lavie, 1997; Cabot and Giuliano, 1997). Adriamycin was used to assess the influence of GCS transfection on cellular response to anthracyclines. After pretreatment with doxycycline for two days, MCF-7/GCS cells were incubated with increasing concentrations of adriamycin for four days. FIG. 14A shows that MCF-7/GCS cells, compared to MCF-7 cells, are resistant to adriamycin toxicity. At 0.5, 1.0, 2.0 and 3.0 $\mu$M adriamycin, survival of transfected MCF-7/GCS cells was significantly greater than that of MCF-7 cells (p<0.0005, FIG. 14A). It was observed that MCF-7/GCS cells were resistant to ceramide toxicity as well. At 2.5 and 5.0 $\mu$M $C_6$-ceramide, MCF-7/GCS cell survival was significantly higher MCF-7 cells (p<0.0005, FIG. 14B). The $EC_{50}$ of adriamycin in MCF-7/GCS cells was approximately 11-times greater than the $EC_{50}$ observed in MCF-7 cells (4.01±0.12 vs. 0.37±0.01 $\mu$M, p<0.0005, FIG. 14C). However, the $EC_{50}$ in the TC group was nearly identical with that of MCF-7 cells, there being no statistical difference between the two groups (FIG. 14C). The $EC_{50}$ of $C_6$-ceramide in MCF-7/GCS cells was 4-fold greater than that observed in MCF-7 cells (12.07±1.50 vs. 3.10±0.50 $\mu$M, p<0.0005, FIG. 14C), and survival of TC cells was not statistically different compared to the parent cell line, MCF-7 (FIG. 14C).

6.13.11. Example 10

Regulation of Ceramide Resistance in MCF-7/GCS Cells

If ceramide resistance is induced by GCS expression in MCF-7/GCS cells, the resistance response should be tightly correlated with the level of the inducer, doxycycline. It was determined that increasing doxycycline concentrations correlated closely with increased expression of GCS, which in turn correlated well with increased resistance of the cells to $C_6$ceramide. After cells were exposed to increasing concentrations of doxycycline, higher expression of GCS mRNA was observed in MCF-7/GCS cells with 1.0 and 3.0 $\mu$g/ml doxycycline (FIG. 15A), the densities being 97 and 256, respectively (GCS band/28 S RNA×100). In contrast, the mRNA was scarcely detectable at 0 and 0.1 $\mu$g/ml doxycycline, with densities measuring 16 and 18, respectively. Only traces of GCS mRNA were found in MCF-7 cells treated with doxycycline (FIG. 15A). GCS activity in MCF-7/GCS cells exposed to 0.1, 1.0, and 3.0 $\mu$g/ml doxycycline was significantly higher than GCS activity observed in MCF-7 cells (p<0.001, FIG. 15B). The r of GCS activity to doxycycline in MCF-7/GCS cells was 0.84. In contrast, increasing amounts of doxycycline did not elevate GCS activity in MCF-7 cells, and the r was 0.48. In concert with enhanced GCS activity, ceramide cytotoxicity in MCF-7/GCS cells was reversed following target gene expression by exposing cells to increasing concentrations of doxycycline. Treatment with $C_6$-ceramide (5 $\mu$M) in conjunction with doxycycline dose escalation, affected a dose-dependent increase in survival of MCF-7/GCS cells, and the survival was significantly higher than that of MCF-7 cells (p<0.001, FIG. 15C). MCF-7/GCS cell survival upon exposure to ceramide was highly correlated with the concentration of doxycycline in the pretreatment regimen (r=0.84 at 0.1–3.0 $\mu$g/ml of doxycycline). In comparing FIG. 15C with FIG. 15B, the increase in cell survival mirrored the induction of GCS activity. The correlation coefficient for these biological parameters was 0.99, verifying that cell survival is closely associated with GCS activity.

6.13.12. Example 11

Adriamycin Induced Hyperglycosylation of Ceramide in MCF-7/GCS Cells

To further define the mechanism of drug resistance in MCF-7/GCS cells, cells were challenged with adriamycin and the metabolism of ceramide was evaluated (FIGS. 16A–16B). As illustrated in FIG. 16A, after 24 and 48 hr exposures to adriamycin, ceramide levels in MCF-7 cells increased 3.4- and 3-fold, respectively; however, in counterpoint, ceramide levels in response to adriamycin in MCF-7/GCS cells increased 1.4- and 1.2-fold at 24 and 48 hr, respectively. Examination of GC metabolism (FIG. 16B) shows that while adriamycin had little impact on GC levels in MCF-7 cells, a time-dependent increase in GC was observed in MCF-7/GCS cells exposed to adriamycin. After 24 and 48 hr with adriamycin, GC levels in the GCS-transfected cells increased 1.4- and 2.1-fold, respectively.

To exclude the possibility that allied factors, such as P-glycoprotein or Bcl-2 (B-cell leukemia oncoprotein) were responsible for conferring ceramide and adriamycin resistance in the transfected cells, the expression of P-glycoprotein and Bcl-2 was measured. Western blot analysis showed that P-glycoprotein was not detected in either MCF-7/GCS or in MCF-7 cells (FIG. 17A), regardless of the absence or presence of doxycycline. Therefore, transfection and inducible expression of GCS did not influence P-glycoprotein levels in MCF-7/GCS cells. Western blot analysis also shows that the phosphorylation/dephosphorylation of Bcl-2 was the same in MCF-7 and in MCF-7/GCS cells, regardless of the absence or presence of doxycycline (FIG. 17B).

GCS was introduced into wild-type MCF-7 breast cancer cells using a retroviral Tet-on expression system. The resulting cell line, MCF-7/GCS, expressed an 11-fold higher level of GCS activity compared to the parental cell line. The transfected cells demonstrated strong resistance to adriamycin and to ceramide, whereas both agents were highly cytotoxic to MCF-7 cells. The $EC_{50}$ values of adriamycin and ceramide were 11-fold (p<0.0005) and 5-fold (p<0.005) higher, respectively, in MCF-7/GCS cells compared to MCF-7 cells. Ceramide resistance displayed by MCF-7/GCS cells closely paralleled the expression of GCS activity with a correlation coefficient of 0.99. In turn, cellular resistance and GCS activity were dependent upon the concentration of expression mediator, doxycycline. Adriamycin resistance in MCF-7/GCS cells was related to the hyperglycosylation of ceramide, and was not related to shifts in the levels of either P-glycoprotein or Bcl-2. These results show that overexpression of GCS, which catalyzes ceramide glycosylation, induces resistance to adraimycin and ceramide in MCF-7 breast cancer cells. In summary, FIG. 18 shows a schematic of the preferred target points in the glycolipid metabolic pathway, specifically the increase in ceramide formation may be caused, for example, by agents on the left, and an inhibition in the conversion of ceramide to glucosylceramide may be caused, for example, by agents on the right. Combination therapies will cause a ceramide increase and/or GC decrease.

The methods of the present invention provide an excellent tool for predicting the effectiveness of chemotherapeutic agents in the treatment of diseases such as cancer. In particular, the methods provide a screening assay for putative chemotherapeutic agents to determine their therapeutic potential efficacy in treatment of cancer. Additionally, the methods of the invention provide for the determination of optimal dosage of, as well as superior combinations of, for example a chemotherapeutic agent and chemosensitizer. Such combinations will allow a therapeutic regime that will be minimally traumatic to the cancer patient. Finally, the methods of the present invention are easily performed, and are therefore time and cost-effective.

The described invention is not limited in scope by the exemplified embodiments which are intended as an illustration for purposes of clarity and understanding, and methods which are functionally equivalent are within the scope of the invention. Various modifications of the invention may become readily apparent to those skilled in the art from the above description and these are intended to fall within the scope of the appended claims.

7. REFERENCES

Ajani, J. A. et. al. (1987) *J. Clin. Oncol.* 5: 1912–1921.
Archinal-Mattheis, A. et. al. (1995) *Oncol. Res.* 7:603–610.
Basu, S., Kaufeman, B., and Roseman, S. (1968) *J. Biol. Chem.* 243, 5802-5804
Bayer, E. A. et. al. (1979) *Meth. Enzym.* 62: 308.
Blagosklonny, M. V., Schulte, T., Nguyen, P., Trepel, J., and Neckers, L. M. (1996) *Cancer Res.* 56:1851–1854.
Bligh, E. G. and Dyer, W. T. (1959). *Canad. J. Biochem. Physiol.* 37: 911–917.
Bogden, A. E. et. al. (1984) *Cancer Res.* 44: 1087–1090.
Bose, R., Verheil, M., Haimovitz-Friedman, A., Scotto K., Fuks Z., and Kolesnick, R. (1995) *Cell* 82, 405–414
Cabot, M. C., and Giuliano, A. E. (1997) *Breast Cancer Res. Treat.* 46(1), 293
Cai, Z., Bettaieb, A., Mahdani, N. E., Legres, L. G., Stancou, R., Masliah, J., and Chouaib, S. (1997) *J. Biol. Chem.* 272, 6918–6926
Cole et. al. (1985) in *Monoclonal Antibodies and Cancer Therapy*, Alan R. Liss, Inc., pp. 77–96
Callaghan, R., and Higgins, C. F. (1995) *Cancer* 71: 294–299.
Campbell, A. M., (1984) *Monoclonal Antibodies Technology: Laboratory Techniques in Biochemistry and Molecular Biology*, Elsevier Science Publishers, Amsterdam, The Netherlands.
Chuma, S. J., Nodzenski, E., Beckett M., A. Kufe D. W., Quintans, J., and Weichselbaum, R. R. (1997) *Cancer Res.* 57, 1270–1275.
Chomczynski, P., and Sacchi, N. (1987)*Anal. Biochem.* 162, 156–159.
Deuchards, K. L. and Ling, V. (1989) *Seminars in Oncology* 16: 156–165.
Engval, E. et. al. (1972) *Immunol.* 109: 129.
Fan, D. et. al. (1994) Reversal of Multidrug Resistance. *CRC. John A. Kellen Book.* Chapter 6, 93–125.
Faris, M., Kokot, N., Lee, L. and Nel, A. (1996) *J. Biol. Chem.* 271, 27366–27373
Foxwell, B. M. et. al. (1989). *Mol. Pharmacol.* 8: 985–994.
Gaveriaux, C. et. al. (1991) *J. Cell Pharmacol.* 2: 225–234.
Goding, J. W. (1976) *J. Immunol. Meth.* 13: 215.
Goseen, M., Freundlieb, S., Bender, G., Muller, G., Hillen, W., and Bujard, H. (1995) *Science* 268, 1766–1769
Gossen, M., and Bujard, H. (1992) *Proc. Natl. Acad. Sci USA* 89, 5547–5551
Grob, R. L. (1995) *Modern practice of Gas Chromotography* 3rd Ed., Wiley-Interscience
Hakomori, S. (1981) *Annu. Rev. Biochem.* 50: 733-764.
Haimovitz-Friedman, A., Kolesnick, R., and Fuks, Z. (1997) *British Medical Bulletin* 53, 539–553
Hannun, Y. (1994) *J. Biol. Chem.* 269: 3125–3128.
Hannun, Y. A. and Bell, R. M. (1989) *Science* 243: 500–507.
Hannun Y. A. and Obeid, L. M. (1995) *Trends. Biochem. Sci.* 20: 73–77.
Harel, R. and Futerman, A. H. (1993) *J. Biol. Chem.* 268: 14476–14481.
Ichikawa, S., Sakiyama, H., Suzuki, G., Hidari, K. I. P., and Hirabayashi, Y. (1996) *Proc. Natl Acad. Sci.* (USA), 93, 4638–4643
Jacoby, W. D. et. al. (1974) *Meth. Enzym.* 34 Academic Press, N.Y.
Jarvis, W. D. et. al. (1996) *Clin. Cancer. Res.* 2: 1–6.
Katz, E. D. (1996) *High Performance Liquid Chromatography: Principles and Methods in Biotechnology*, Katz, E. D. Ed., Perkin-Elmer Corporation, Norwalk, Conn.
Katz, E. D. (1987) *Quantitative Analysis using Chromatographic Techniques* Katz, E. D. Ed., Perkin-Elmer Corporation, Norwalk, Conn.
Kohler, G. and Milstein, C. (1975) *Nature* 256:495–497.
Kolesnick, R. and Golde, D. W. (1994) *Cell* 77: 325–328.
Kozbor, D. et. al. (1983) *Immunology Today* 4:72.
Kratzke, R. A. and Kramer, B. S. (1996) *J. Cell Biochem. Suppl.* 24: 160–164.
Krul, (1994) *Emerging Resources,* Decision Resources, Inc. pp. 79–94.
Lavie, Y., Cao, H. T., Volner, A., Lucci, A., Han, T. Y., Geffen, V., Giuliano, A. E., and Cabot, M. C. (1997) *J. Biol. Chem.* 272, 1682-1687.
Lavie Y. et. al. (1996) *J. Biol. Chem.* 271: 19530–19536.
Lucci, A. et. al. "Glucosylceramide: A Marker for Multiple Drug Resistant Cancers" (submitted for publication). This work was presented at the 50$^{th}$ Annual Meeting of the Society of Surgical Oncology, Mar. 20–23, 1997, Chicago.
Lutz et. al.(1988) *Exp. Cell Research.* 175: 109–124.
Michael, J. M., Lavin, M. F., and Watters, D. J. (1997) *Cancer Res.* 57, 3600–3605
Morton, D. L. et. al. (1994) *Prog. Brain Res.* 101: 251–275.
Nakamura, S. et. al. (1996) *J. Biol. Chem.* 271: 1255–1257.
Noso, Y. et. al. (1987) *Cancer Res.* 47: 6418–6422.
Obeid, L. M. et. al. (1993) *Science* 259: 1769–1771.
Pastan, I. and Gottesman, M. (1987) *New Engl. J. Med.* 316:1388–1393.
Patonay, G. (1992) *HPLC Detection: Newer Methods*, Wiley VCH.
Pena, L. A. et. al. (1997) *Biochem. Pharmacol.* 53: 615–621.
Rani, C. S. S. et. al. (1995) *J. Biol. Chem.* 270: 2859–2867.
Resnitzky, D., Gossen, M., Bujard, H., and Reed, S. I. (1994) *Mol. Cell Biol.* 14, 1669–1679
Sambrook, J. et al., (1989) *Molecular Cloning: a Laboratory Manual.* 2nd Ed. cold spring Harbor Laboratory, Cold spring Harbor, N.Y.
Shayman, J. A., Deshmukh, G. D., Mahdiyoun, S., Thomas, T. P., Wu, D., Barcelon, F. S. and Radin, N. S. (1991) *J. Biol. Chem.* 266, 22968–22974

Santana, P., Pena, L. A., Haimovitz-Friedman, A., Martin, S., Green, D., McLoughlin, M., Cordon-Cardo, C., Schuchman, E. H., Fuks, Z., and Kolesnick, R. (1996) *Cell* 86, 189–199

Schwarz, A. et. al. (1995) *J. Biol. Chem.* 270: 10990–10998.

Shoemaker, R. H. et. al. (1985) *Cancer Res.* 45: 2145–2153.

Shukla, G. S., and Radin, N. S. (1990) *Arch. Biochem. Biophys.* 293, 372–378

Snyder, L. R. et. al. (1997) *Practical HPLC Method Development* 2nd Ed., Wiley-VCH.

Sternberger, L. A. et. al.(1970) *J. Histochem. Cytochem.* 18: 315.

Smyth, M. J, Obeid, L. M., and Hannun, Y. A. (1997) *Adv. Pharm.* 41, 133–154

Testi, R. (1996) *Trends Biochem. Sci.* 21, 468–471

Touchstone, J. C. (1992) *Practice of Thin-Layer Chromatography*, 3rd ed., Wiley-Interscience.

Watanabe, T et. al. (1995) *Acta Oncologica* 34: 235–241.

Weir, D. M. et. al. (1986) *"Handbook of Experimental Immunology"* 4th Ed., Blackwell Scientific Publications, Oxford, England, Chapter 10.

Weisenthal, L. M. et. al. (1983) *Cancer Res.* 43: 258–264.

Wyllie, A. H. (1997) *Eur. J. Cell Biol.* 73: 189–197.

Yang, J. M. etal., (1996) *Cancer research* 56:3490–3494.

Yau, W. W. et. al. (1979) *Modern Size-Exclusion Liquid Chromatography: Practice of Gel Permeation and Gel Filtration Chromatography,* duPont de Nemours & Company, Wilmington, Del.

Yin, D. X., Zhu, L., and Schimke, R. T. (1996) *Anal. Biochem.* 235, 195–201 Grob, R. L. (1995) *Modern Practice of Gas Chromatography* 3rd Ed., Wiley-Interscience Yuhas, J. M. et. al. (1978) *Cancer Res.* 38: 3595–3598.

Yusa, K., and Tsuruo, T. (1989) *Cancer Res.* 49: 5002–5006

Zyad, A., Benard, J., Tursz, T., Clarke, R., and Chouaib, S. (1994) *Cancer Res.* 54, 825-831.

What is claimed is:

1. A method for assessing the therapeutic potential of a chemotherapeutic agent in a combination with a chemosensitizer for treating a disease, said method comprising:

(a) contacting cells expressing glucosylceramide synthase (GCS) with a combination of at least one chemotherapeutic agent and at least one chemosensitizer; and (b) measuring the activity of GCS in said cells, wherein a decrease in said GCS activity indicates therapeutic potential of said combination in treating said disease.

2. The method of claim 1 wherein said cells are cancer cells.

3. The method of claim 2 wherein said cancer cells are selected from the group consisting of breast cancer cell, lymphoma cell, melanoma cell, sarcoma cells, leukemia cells, retinoblastoma cells, hepatoma cells, myeloma cells, glioma cells, mesothelioma cells or carcinoma cells.

4. The method of claim 1 wherein said cells are a cultured cell line.

5. The method of claim 4 wherein said disease is characterized by inappropriate cellular proliferation.

6. The method of claim 5, wherein said disease is cancer or an autoimmune disease.

7. The method of claim 1, wherein said chemosensitizer effects sphingolipid biosynthesis or generation.

* * * * *